United States Patent
Tzeng et al.

(10) Patent No.: US 6,589,271 B1
(45) Date of Patent: Jul. 8, 2003

(54) INDWELLING HEAT EXCHANGE CATHETER

(75) Inventors: Elbert Tzeng, Irvine, CA (US); Vaso Adzich, Yorba Linda, CA (US); Hortensia Pompa, San Clemente, CA (US); Scott M. Evans, Santa Ana, CA (US); Peter Barker, Oceanside, CA (US); William J. Worthen, Coto de Caza, CA (US); Suzanne C. Winter, Coto de Caza, CA (US); David P. Balding, Mission Viejo, CA (US); Kenneth A. Collins, Mission Viejo, CA (US)

(73) Assignee: Alsius Corporations, Irvine, CA (US)

( * ) Notice: Subject to any disclaimer, the term of this patent is extended or adjusted under 35 U.S.C. 154(b) by 0 days.

(21) Appl. No.: 10/015,505

(22) Filed: Dec. 13, 2001

Related U.S. Application Data

(63) Continuation-in-part of application No. 09/503,014, filed on Feb. 11, 2000, now Pat. No. 6,409,747, which is a continuation of application No. 09/063,984, filed on Apr. 21, 1998, now Pat. No. 6,126,684, which is a continuation-in-part of application No. 09/540,693, filed on Mar. 31, 2000, which is a division of application No. 09/375,079, filed on Aug. 16, 1999, now Pat. No. 6,149,670, which is a continuation-in-part of application No. 09/266,452, filed on Mar. 11, 1999, now Pat. No. 6,458,150, which is a continuation-in-part of application No. 09/253,109, filed on Feb. 19, 1999, now abandoned, which is a continuation-in-part of application No. 09/063,984, filed on Apr. 21, 1998, now Pat. No. 6,126,684, which is a continuation-in-part of application No. 09/565,039, filed on May 3, 2000, now Pat. No. 6,432,124, which is a continuation of application No. 09/375,079, filed on Aug. 16, 1999, now Pat. No. 6,149,670, which is a continuation-in-part of application No. 09/266,452, filed on Mar. 11, 1999, now Pat. No. 6,458,150, which is a continuation-in-part of application No. 09/253,109, filed on Feb. 19, 1999, now abandoned, which is a continuation-in-part of application No. 09/063,984, filed on Apr. 21, 1998, now Pat. No. 6,126,684.

(51) Int. Cl.$^7$ ................................................ A61F 7/00
(52) U.S. Cl. ........................ 607/105; 607/106; 607/113
(58) Field of Search ............................... 607/104–106, 607/113; 606/20–23, 27–28; 604/113

(56) References Cited

U.S. PATENT DOCUMENTS 2,058,780 A 10/1936 Elliot (List continued on next page.)

FOREIGN PATENT DOCUMENTS

WO  WO 98/26831  6/1998

(List continued on next page.)

OTHER PUBLICATIONS

U.S. patent application Ser. No. 09/477,490, Lasersohn et al., App Pending.

(List continued on next page.)

*Primary Examiner*—Roy D. Gibson
(74) *Attorney, Agent, or Firm*—John L. Rogitz

(57) ABSTRACT

Catheters adapted to exchange heat with a body fluid flowing through a body conduit employ helical elongate lumens for heat transfer with the body fluid. The helical elongate lumen of a catheter forms multiple turns extending longitudinally of a portion of the catheter with the turns each being bonded to the catheter along a fraction of the length of the turn. The length of the lumen and its orientation in each turn has the lumen otherwise displaced over a major portion of its length from the elongate body. The turns of the helical lumen can be arranged in sets having different lengths to encounter all areas of the flow. One or more infusion lumens may also extend to an infusion port or ports. The helical elongate lumen is defined by an elongate, thin-walled element. This lumen is in fluid communication with a heater/chiller supplying a working fluid for heat transfer through the wall of the elongate element defining the helical elongate lumen. A proximal hub may be associated with the catheter to establish at least one suture anchor and to receive the heater/chiller flow through input and output lumens associated with the catheter and in fluid communication with the helical elongate lumens. The elongated lumens may also be arranged in non-helical arrangements such as in a semi-circular configuration, a figure-eight loop configuration or a random loop configuration.

48 Claims, 18 Drawing Sheets

U.S. PATENT DOCUMENTS

| | | |
|---|---|---|
| 2,077,453 A | 4/1937 | Albright |
| 2,308,484 A | 1/1943 | Auzin et al. |
| 3,125,096 A | 3/1964 | Antiles et al. |
| 3,142,157 A | 7/1964 | Podolsky |
| 3,238,944 A | 3/1966 | Hirschhorn |
| 3,282,267 A | 11/1966 | Eidus |
| 3,327,713 A | 6/1967 | Eidus |
| 3,425,419 A | 2/1969 | Dato |
| 3,504,674 A | 4/1970 | Swenson et al. |
| 3,738,372 A | 6/1973 | Shioshvili |
| 3,776,241 A | 12/1973 | Magilton et al. |
| 3,897,790 A | 8/1975 | Magilton et al. |
| 3,913,581 A | 10/1975 | Ritson et al. |
| 4,010,795 A | 3/1977 | Stenberg |
| 4,111,209 A | 9/1978 | Wolvek et al. |
| 4,154,245 A | 5/1979 | Daily |
| 4,249,923 A | 2/1981 | Walda |
| 4,298,006 A | 11/1981 | Parks |
| 4,416,280 A | 11/1983 | Carpenter et al. |
| 4,416,281 A | 11/1983 | Cooper et al. |
| 4,583,969 A | 4/1986 | Mortensen |
| 4,672,962 A | 6/1987 | Hershenson |
| 4,745,922 A | 5/1988 | Taylor |
| 4,748,979 A | 6/1988 | Hershenson |
| 4,750,493 A | 6/1988 | Brader |
| 4,754,752 A | 7/1988 | Ginsburg et al. |
| 4,759,349 A | 7/1988 | Betz et al. |
| 4,791,930 A | 12/1988 | Suzuki et al. |
| 4,813,210 A | 3/1989 | Masuda et al. |
| 4,823,076 A | 4/1989 | Haines et al. |
| RE32,983 E | 7/1989 | Levy |
| 4,844,074 A | 7/1989 | Kurucz |
| 4,850,958 A | 7/1989 | Berry et al. |
| 4,860,744 A | 8/1989 | Johnson et al. |
| 4,883,455 A | 11/1989 | Leonard |
| 4,899,741 A | 2/1990 | Bentley et al. |
| 4,920,963 A | 5/1990 | Brader |
| 4,987,896 A | 1/1991 | Nakamatsu |
| RE33,561 E | 3/1991 | Levy |
| 5,019,075 A | 5/1991 | Spears et al. |
| 5,021,045 A | 6/1991 | Buckberg et al. |
| 5,037,383 A | 8/1991 | Vaslef et al. |
| 5,041,089 A | 8/1991 | Mueller et al. |
| 5,066,578 A | 11/1991 | Wikman-Coffelt |
| 5,078,713 A | 1/1992 | Varney |
| 5,092,841 A | 3/1992 | Spears |
| 5,098,376 A | 3/1992 | Berry et al. |
| 5,106,360 A | 4/1992 | Ishiwara et al. |
| 5,139,496 A | 8/1992 | Hed |
| 5,147,355 A | 9/1992 | Friedman et al. |
| 5,147,385 A | 9/1992 | Beck et al. |
| 5,151,100 A | 9/1992 | Abele et al. |
| 5,158,534 A | 10/1992 | Berry et al. |
| 5,174,285 A | 12/1992 | Fontenot |
| 5,182,317 A | 1/1993 | Winters et al. |
| 5,191,883 A | 3/1993 | Lennox et al. |
| 5,196,024 A | 3/1993 | Barath |
| 5,211,631 A | 5/1993 | Sheaff |
| 5,230,862 A | 7/1993 | Berry et al. |
| 5,248,312 A | 9/1993 | Langberg |
| 5,250,070 A | 10/1993 | Parodi |
| 5,257,977 A | 11/1993 | Eshel |
| 5,261,399 A | 11/1993 | Klatz et al. |
| 5,262,451 A | 11/1993 | Winters et al. |
| 5,269,758 A | 12/1993 | Taheri |
| 5,275,595 A | 1/1994 | Dobak, III et al. |
| 5,279,598 A | 1/1994 | Sheaff |
| 5,281,213 A | 1/1994 | Milder et al. |
| 5,281,215 A | 1/1994 | Milder |
| 5,324,286 A | 6/1994 | Fowle |
| 5,338,770 A | 8/1994 | Winters et al. |
| 5,342,301 A | 8/1994 | Saab |
| 5,342,693 A | 8/1994 | Winters et al. |
| 5,354,277 A | 10/1994 | Guzman et al. |
| 5,411,477 A | 5/1995 | Saab |
| 5,423,807 A | 6/1995 | Milder |
| 5,437,673 A | 8/1995 | Baust et al. |
| 5,452,582 A | 9/1995 | Longsworth |
| 5,478,309 A | 12/1995 | Sweezer et al. |
| 5,486,204 A | 1/1996 | Clifton |
| 5,486,208 A | 1/1996 | Ginsburg |
| 5,531,776 A | 7/1996 | Ward et al. |
| 5,545,161 A | 8/1996 | Imran |
| 5,562,606 A | 10/1996 | Huybregts |
| 5,609,620 A | 3/1997 | Daily |
| 5,624,392 A | 4/1997 | Saab |
| 5,655,548 A | 8/1997 | Nelson et al. |
| 5,656,420 A | 8/1997 | Chien |
| 5,693,080 A | 12/1997 | Wallsten et al. |
| 5,702,435 A | 12/1997 | Maytal |
| 5,716,386 A | 2/1998 | Ward et al. |
| 5,733,319 A | 3/1998 | Neilson et al. |
| 5,735,809 A | 4/1998 | Gorsuch |
| 5,758,505 A | 6/1998 | Dobak, III et al. |
| 5,759,182 A | 6/1998 | Varney et al. |
| 5,787,715 A | 8/1998 | Dobak, III et al. |
| 5,837,003 A | 11/1998 | Ginsburg |
| 5,957,962 A | 9/1999 | Wallsten |
| 6,019,783 A | 2/2000 | Philips et al. |
| 6,042,559 A | 3/2000 | Dobak, III |
| 6,051,019 A | 4/2000 | Dobak, III |
| 6,096,068 A | 8/2000 | Dobak, III |
| 6,110,168 A | 8/2000 | Ginsburg |
| 6,149,670 A | 11/2000 | Worthen et al. |
| 6,149,673 A | 11/2000 | Ginsburg |
| 6,149,676 A | 11/2000 | Ginsburg |
| 6,149,677 A | 11/2000 | Dobak, III |
| 6,224,624 B1 | 5/2001 | Lasheras et al. |
| 6,231,595 B1 | 5/2001 | Dobak, III |
| 6,235,048 B1 | 5/2001 | Dobak, III |
| 6,238,428 B1 | 5/2001 | Werneth et al. |
| 6,245,095 B1 | 6/2001 | Dobak, III et al. |
| 6,251,129 B1 | 6/2001 | Dobak, III et al. |
| 6,251,130 B1 | 6/2001 | Dobak, III et al. |
| 6,254,626 B1 | 7/2001 | Dobak, III et al. |
| 6,261,312 B1 | 7/2001 | Dobak, III et al. |
| 6,264,679 B1 | 7/2001 | Keller et al. |
| 6,306,161 B1 | 10/2001 | Ginsburg |
| 6,312,452 B1 | 11/2001 | Dobak, III et al. |
| 6,325,818 B1 | 12/2001 | Werneth |
| 6,393,320 B2 | 5/2002 | Lasersohn et al. |
| 2001/0001830 A1 | 5/2001 | Dobak, III et al. |
| 2001/0001832 A1 | 5/2001 | Dobak, III et al. |
| 2001/0005791 A1 | 6/2001 | Ginsburg et al. |
| 2001/0007951 A1 | 7/2001 | Dobak, III et al. |
| 2001/0008975 A1 | 7/2001 | Dobak, III et al. |
| 2001/0011185 A1 | 8/2001 | Dobak, III et al. |
| 2001/0016763 A1 | 8/2001 | Lasheras et al. |
| 2001/0016764 A1 | 8/2001 | Dobak, III |
| 2001/0021865 A1 | 9/2001 | Dobak, III et al. |
| 2001/0021866 A1 | 9/2001 | Dobak, III et al. |
| 2001/0029394 A1 | 10/2001 | Dobak, III et al. |
| 2001/0041923 A1 | 11/2001 | Dobak, III |
| 2001/0047196 A1 | 11/2001 | Ginsburg et al. |

FOREIGN PATENT DOCUMENTS

| | | |
|---|---|---|
| WO | WO 98/31312 | 7/1998 |
| WO | WO 01/43611 | 6/2001 |

OTHER PUBLICATIONS

U.S. patent application Ser. No. 09/540,693, Worthen et al., App Pending.

U.S. patent application Ser. No. 09/565,039, Worthen et al., App Pending.

U.S. patent application Ser. No. 09/822,984, Worthen et al., App Pending.

U.S. patent application Ser. No. 09/911,369, Lasersohn et al., App Pending.

U.S. patent application Ser. No. 09/911,370, Lasersohn et al., App Pending.

U.S. patent application Ser. No. 10/100,555, Worthen et al., App Pending.

U.S. patent application Ser. No. 10/057,334, Aliberto et al., App Pending.

U.S. patent application Ser. No. 10/061,488, Evans et al., App Pending.

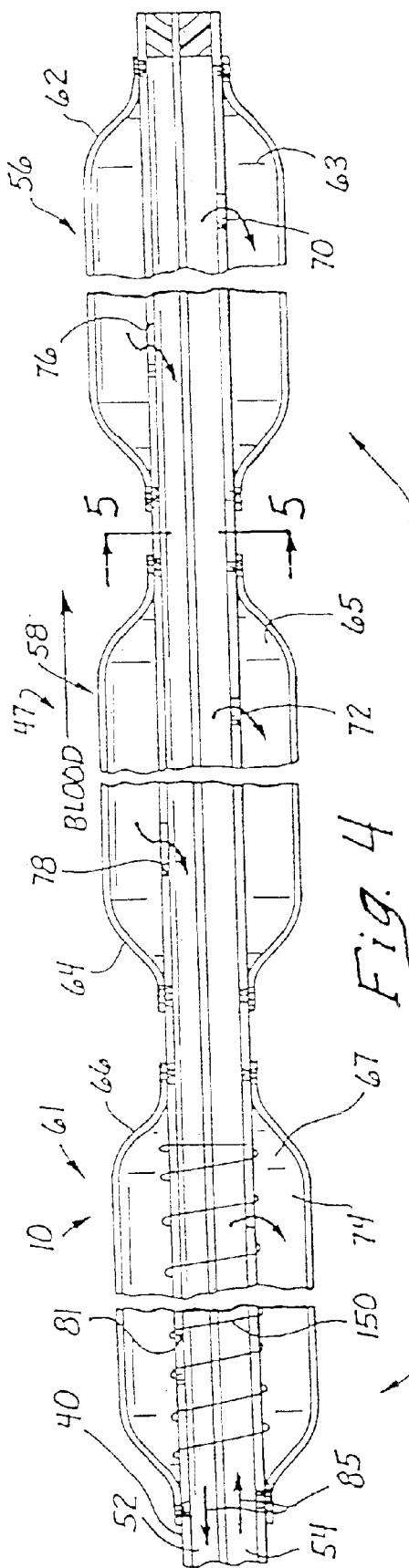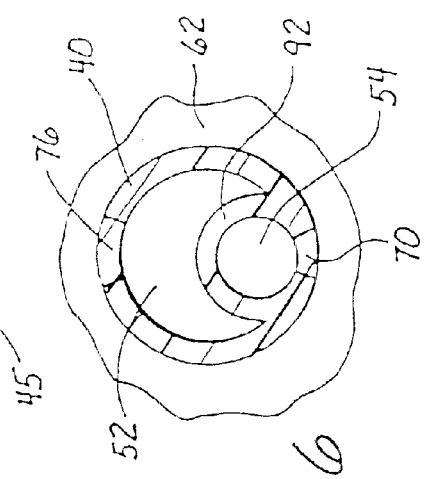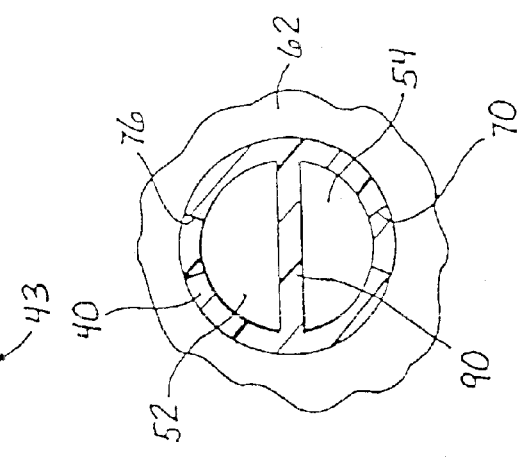

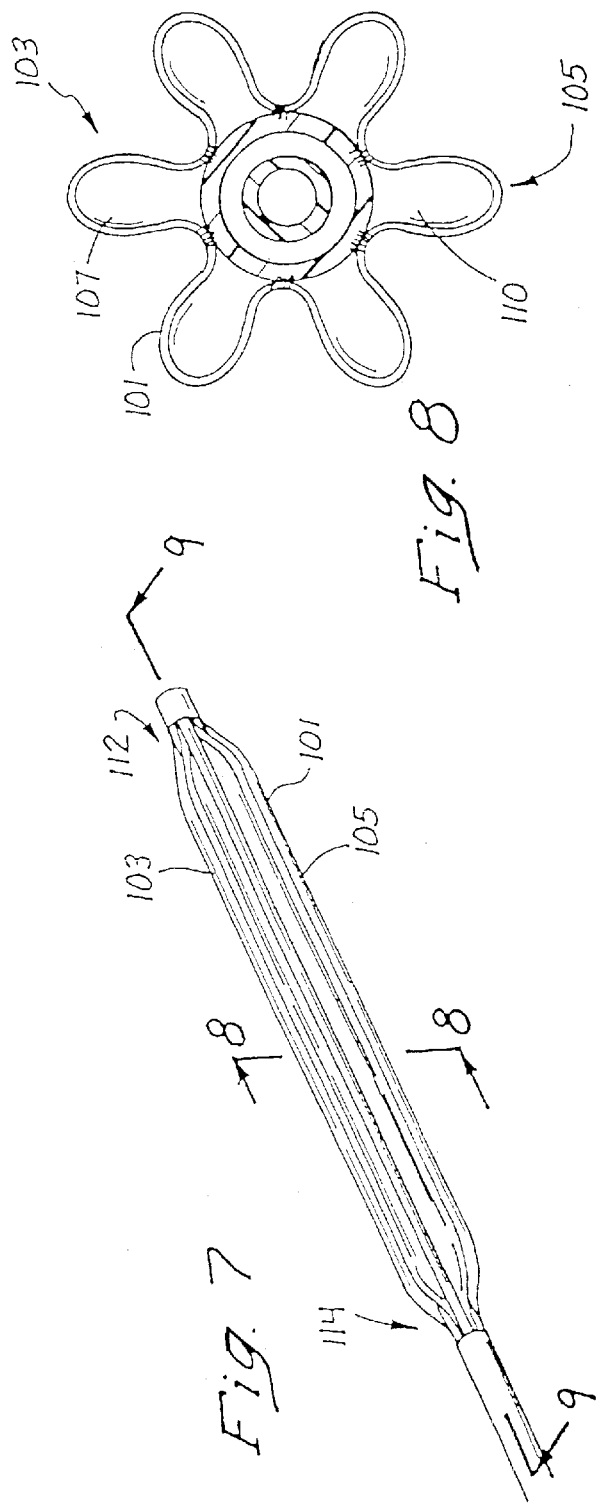
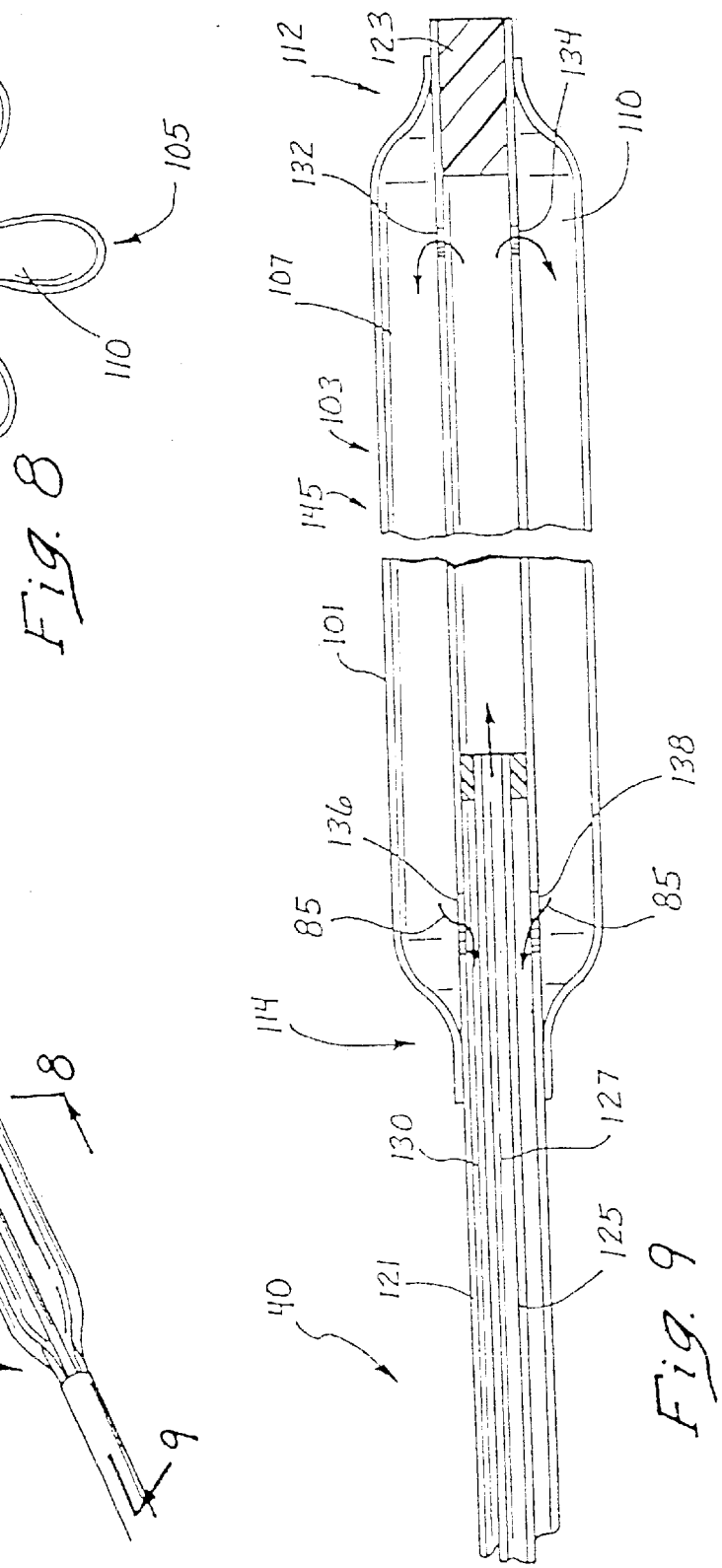

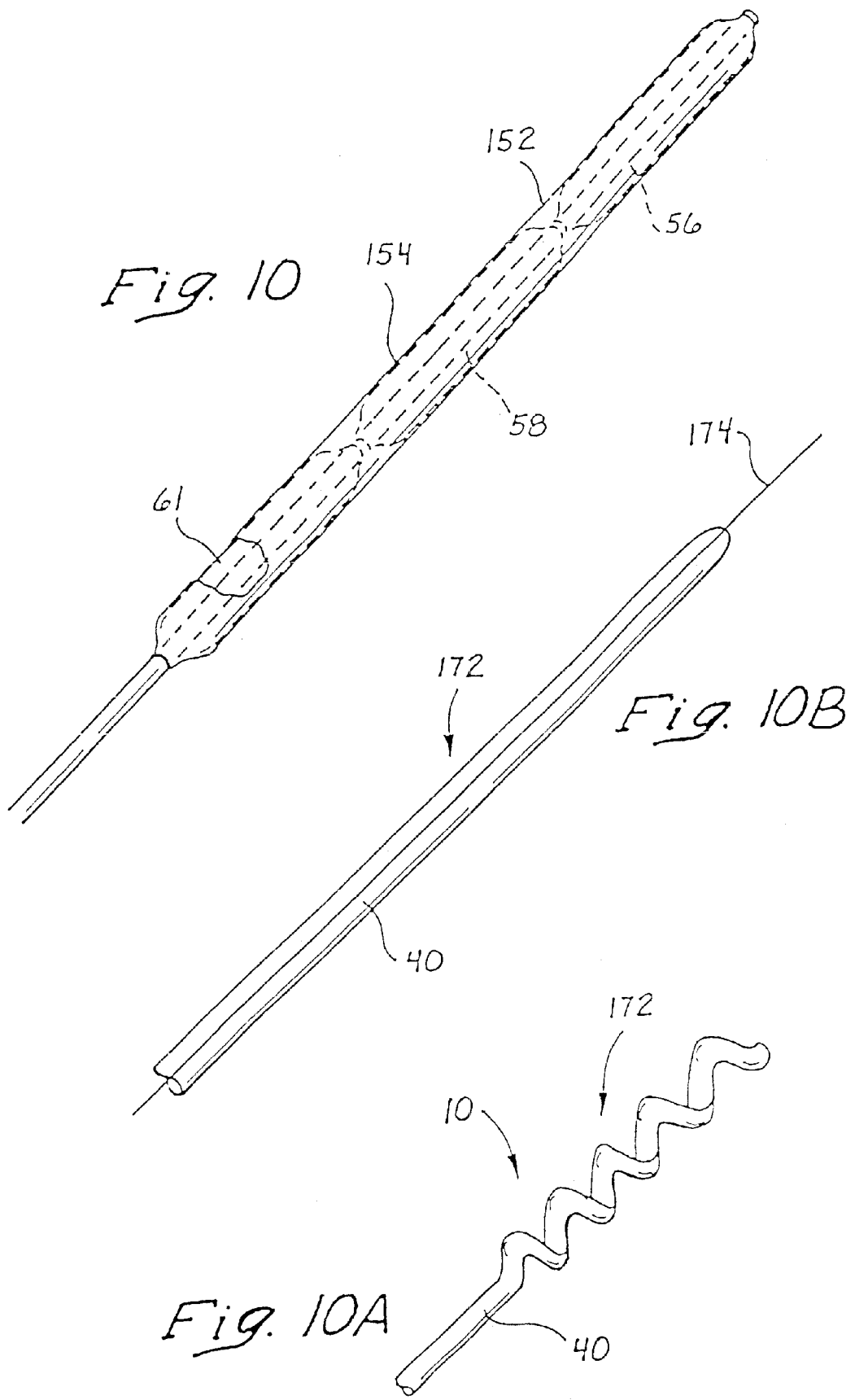

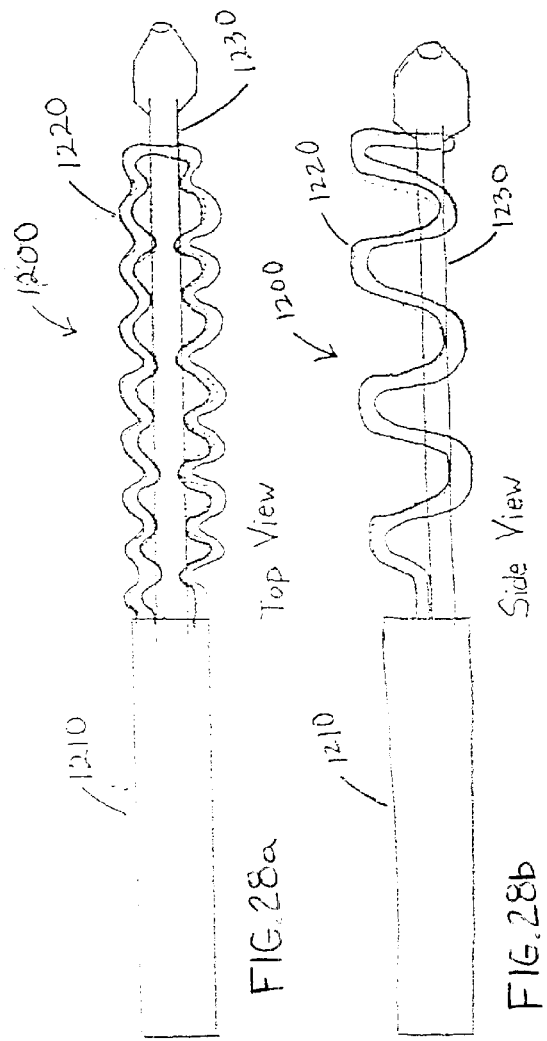

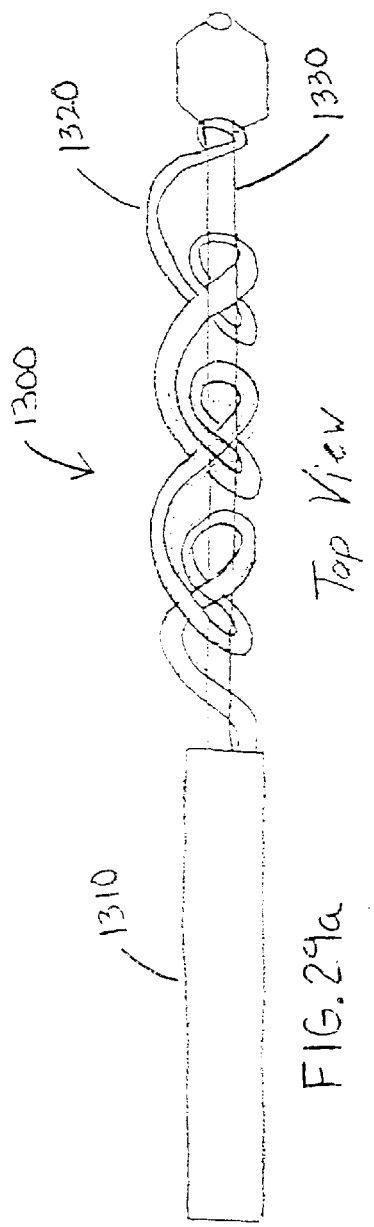
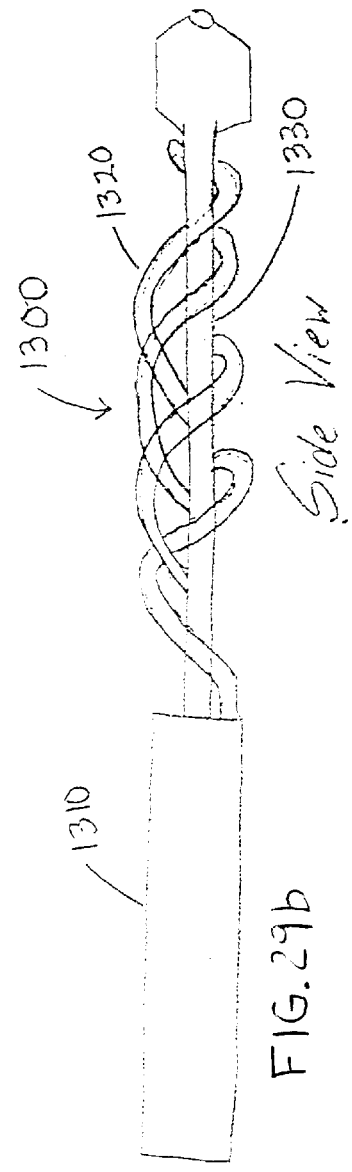
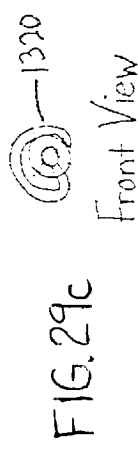

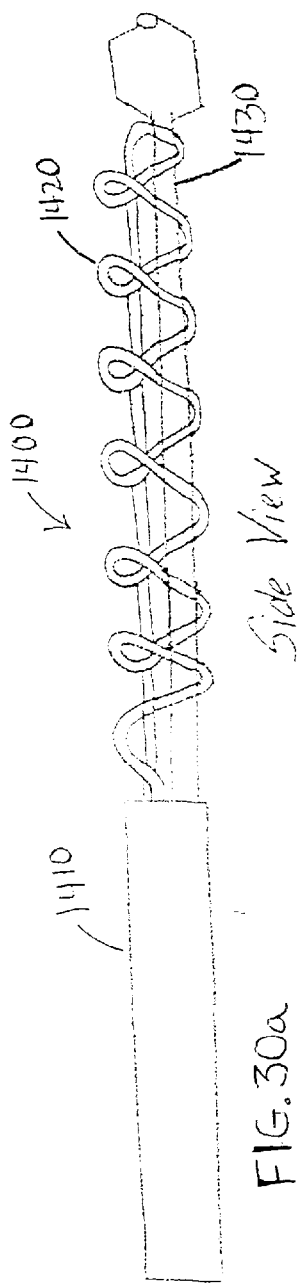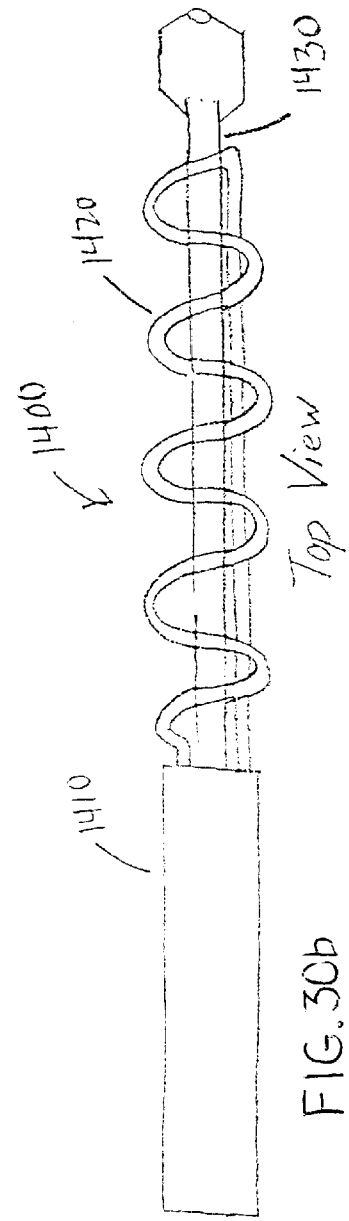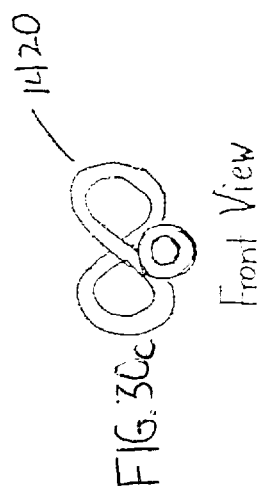
FIG. 30a Side View
FIG. 30b Top View
FIG. 30c Front View

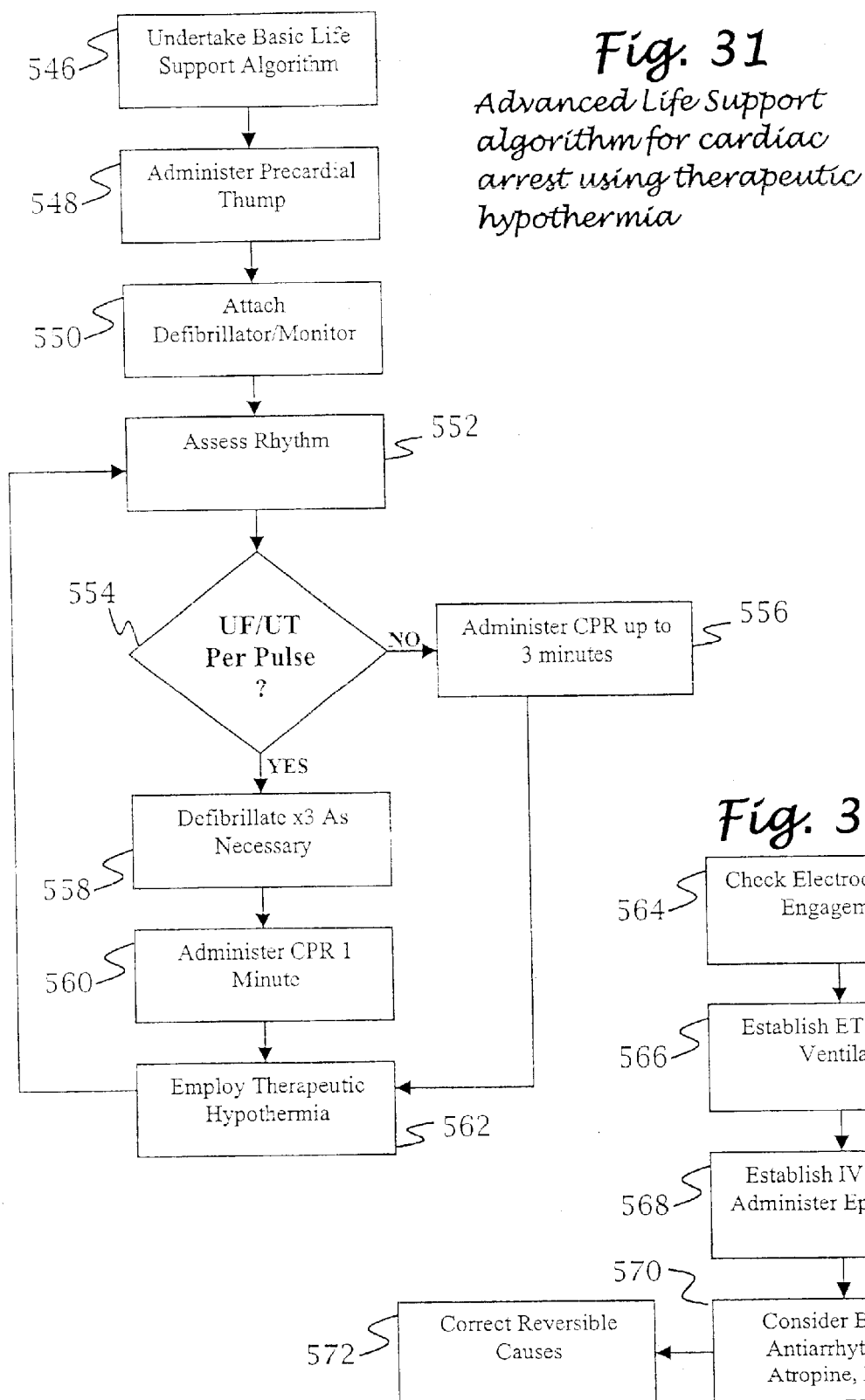
Fig. 31
Advanced Life Support algorithm for cardiac arrest using therapeutic hypothermia
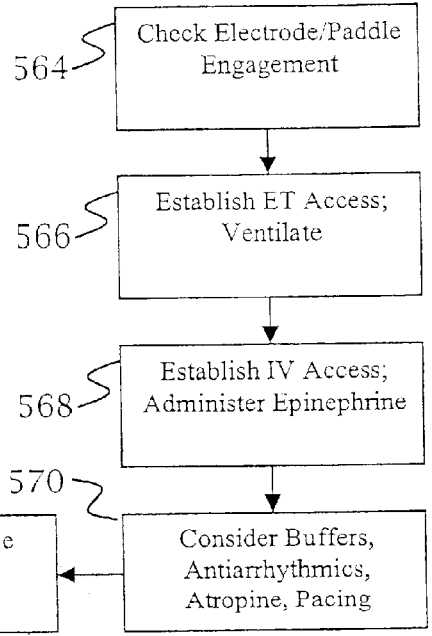
Fig. 32 CPR

INDWELLING HEAT EXCHANGE CATHETER

CROSS-REFERENCE TO RELATED APPLICATION

The present application is a continuation-in-part of U.S. patent application Ser. No. 09/503,014 filed on Feb. 11, 2000, U.S. Pat. No. 6,409,747 which is a continuation U.S. application Ser. No. 09/063,984 filed on Apr. 21, 1998, now issued as U.S. Pat. No. 6,126,684, the disclosures of which are herein incorporated by reference in their entirety; and further, the present application is a continuation-in-part of U.S. patent application Ser. No. 09/540,693 filed on Mar. 31, 2000, which is a divisional of U.S. patent application Ser. No. 09/375,079 filed on Aug. 16, 1999, now issued as U.S. Pat. No. 6,149,670, which is a continuation-in-part of U.S. patent application Ser. No. 09/266,452 filed on Mar. 11, 1999, U.S. Pat. No. 6,458,150 which is a continuation-in-part of U.S. patent application Ser. No. 09/253,109 filed on Feb. 19, 1999, abandoned which is a continuation-in-part of U.S. patent application Ser. No. 09/063,984 filed on Apr. 21, 1998, now issued as U.S. Pat. No. 6,126,684, the disclosures of which are herein incorporated by reference in their entirety; and further, the present application is a continuation-in-part of U.S. patent application Ser. No. 09/565,039 filed on May 3, 2000, U.S. Pat. No. 6,432,124 which is a continuation of U.S. patent application Ser. No. 09/375,079 filed on Aug. 16, 1999, now issued as U.S. Pat. No. 6,149,670, which is a continuation-in-part of U.S. patent application Ser. No. 09/266,452 filed on Mar. 11, 1999, U.S. Pat. No. 6,458,150 which is a continuation-in-part of U.S. patent application Ser. No. 09/253,109 filed on Feb. 19, 1999, abandoned which is a continuation-in-part of U.S. patent application Ser. No. 09/063,984 filed on Apr. 21, 1998, now issued as U.S. Pat. No. 6,126,684, the disclosures of which are herein incorporated by reference in their entirety.

BACKGROUND OF THE INVENTION

The field of the present invention is heat transfer catheters for heating and cooling body fluid.

The advantageous use of hypothermia in medical procedures is known. For example, a reduction in metabolic rate of a body may be achieved through the lowering of body temperature. Reduced metabolism makes it possible to more easily accommodate lengthy operative procedures. In stroke, trauma and several other pathological conditions, hypothermia also reduces the permeability of the blood/brain barrier. It inhibits release of damaging neurotransmitters and also inhibits calcium-mediated effects. Further, hypothermia inhibits brain edema and lowers intracranial pressure. Improvements have been observed for patients suffering from severe brain trauma or from ischemia caused by stroke or heart attack when the patient is cooled below normal body temperature (38° C.).

Hypothermic treatment has been typically addressed systemically, meaning that the overall temperature of the entire body is lowered. A cooling device used systemically in the circulatory system is known to be more efficient than external methods such as cooling blankets, ice water, bladder lavages, ice baths, esophageal catheters since the entire volume of the body is constantly perfused with the cold fluid at a capillary level.

In other medical situations, it may be desirable to raise the patient's body temperature. For example, a patient may suffer from unintended hypothermia and may need to be warmed to a normothermic temperature. These results can be obtained by intravascular heating through a heat exchange catheter.

Heat exchange catheters are also used to create hypothermia and hyperthermia in a patient or in selected portions of the patient's body. Systems capable of such operation are illustrated by Gobin et al. in U.S. Pat. No. 6,126,684, the disclosure of which is incorporated herein by reference.

As understood by the present invention, cooling blankets, lavages and the like are cumbersome and time consuming to use and manage. The present invention provides the solutions noted below.

SUMMARY OF THE INVENTION

The present invention is directed to catheters adapted to exchange heat with a body fluid flowing through a body conduit. The catheters employ at least one elongate lumen forming multiple turns for heat transfer with the body fluid.

In a first separate aspect of the present invention, the catheter shaft includes an axis, a fluid inlet lumen and a fluid outlet lumen each extending generally between a proximal end and a distal end of the shaft. A hub disposed at the proximal end provides access to the fluid lumens. At least one balloon is provided in a heat exchange region at the distal end of the shaft, the balloon wall providing the barrier between the two fluids. With the catheter positioned in contact with the body fluid within the conduit, heat transfer occurs across the balloon wall. The relative temperature differential is facilitated with countercurrent flow between the two fluids.

In a second separate aspect of the invention, a first balloon is disposed at the distal end of the shaft and defines with the shaft an inflatable first cavity. Portions of the shaft define a first inlet hole extending in fluid communication between the first lumen and the first cavity. Portions of the shaft define a first outlet hole extending in fluid communication between the first cavity and the fluid outlet lumen. A second balloon disposed relative to the first balloon defines with the shaft an inflatable second cavity with portions of the shaft defining a second inlet hole between the fluid inlet lumen and the second cavity. Portions of the shaft also define a second outlet hole in fluid communication with the second cavity and the fluid outlet lumen. Typically, the first balloon will be disposed distally of the second balloon and the first inlet hole will be larger than the second inlet hole. As elastomeric material covering a valley or volume between the first balloon and the second balloon may be provided to promote mixing necessary for efficient heat exchange yet minimize turbulence and shear which can be damaging to blood.

In a third separate aspect of the invention, a method for exchanging heat with a body fluid in a body conduit includes the step of introducing into the body conduit a catheter having an inlet lumen and an outlet lumen. The catheter is provided with a first cavity and a second cavity each in heat transfer relationship with the body fluid in the body conduit. A heat exchange fluid is introduced into the inlet lumen and through an inlet hole into each of the first cavity and the second cavity. An exchange of heat then occurs between the heat exchange fluid in the first and second cavities and the body fluid in the body conduit. Ultimately, the heat exchange fluid is removed through an outlet hole and the outlet lumen associated with each of the first cavity and the second cavity. Creating non laminar flow in one or both of the heat exchange fluid and the body fluid will improve heat transfer efficiency. Heat transfer can also be effected by various structures which either enhance or inhibit turbulence in the fluids.

In a fourth separate aspect of the present invention, the elongate lumen forms multiple turns with the turns each having a length and being bonded to the catheter along a fraction of that length. The length of the lumen and its orientation in each turn has the lumen otherwise displaced from the elongate body. Thus, body fluid can flow freely about each turn of the lumen with the exception of the fractions of length where the lumen is attached to the catheter.

In a fifth separate aspect of the present invention, the elongate lumen is helical and forms multiple turns and extends longitudinally along a portion of the catheter. The length of the lumen and its orientation in each turn has the lumen otherwise displaced from the elongate body. Thus, body fluid can flow freely about each turn of the lumen with the exception of the fractions of length where the lumen is attached to the catheter.

In a sixth separate aspect of the present invention, the elongate lumen is displaced over a major portion of its length from the body of the catheter. The turns of the lumen can be arranged in sets having different lengths to encounter all areas of the flow.

In a seventh separate aspect of the present invention, the elongate lumen is principally displaced from the catheter body for efficient body fluid flow about the lumen. One or more infusion lumens may also extend to an infusion port or ports, advantageously operating with the helical elongate lumen to better distribute infusions within the stream of the body fluid.

In an eighth separate aspect of the present invention, the elongate lumen is defined by an elongate element principally displaced from the elongate body of the catheter. The elongate element is thin-walled and collapsible under fluid pressure of the body fluid when the flow through the lumen is not induced. The thin-wall provides flexibility for an initially collapsed position of the helical elongate lumen for insertion, its expansion under pressure and subsequent and partial collapse for extraction and provides efficient heat transfer across the wall of the element.

In a ninth separate aspect of the present invention, the elongate lumen, defined by an elongate element forming a helical and axially extending configuration, is principally displaced from the elongate body of the catheter for fluid body flow about the lumen along most of its length. The body of the catheter includes an input lumen and an output lumen in fluid communication with the helical elongate lumen. The elongate element defining the helical elongate lumen has a substantially equal cross-sectional area to that of the input lumen such that the elongate element can be fitted with the input lumen.

In a tenth separate aspect of the present invention, the elongate lumen is arranged to be displaced along a substantial portion of its length from the catheter. This lumen is in fluid communication with a heater/chiller supplying a working fluid for heat transfer through the wall of the elongate element defining a helical elongate lumen. A proximal hub may be associated with the catheter to establish at least one suture anchor. Further, the hub may receive the heater/chiller flow through input and output lumens associated with the catheter and in fluid communication with the helical elongate lumens.

In an eleventh separate aspect of the present invention, a method for treating cardiac arrest in a patient is contemplated.

In a twelfth separate aspect of the present invention, a method for treating myocardial infarction in a patient is contemplated.

In a thirteenth separate aspect of the present invention, combinations of any of the foregoing aspects and features are contemplated.

Accordingly, it is an object of the present invention to provide improved heat transfer catheters. Other and further objects and advantages will appear hereinafter.

BRIEF DESCRIPTION OF THE DRAWINGS

FIG. 4 is an enlarged axial cross section view of a plurality of balloons disposed in the heat exchange region of the catheter;

FIG. 5 is a radial cross section view of the catheter taken along lines 5—5 of FIG. 4;

FIG. 6 is a radial cross section view similar to FIG. 5 of a further embodiment of the catheter;

FIG. 7 is a perspective view of a further embodiment of the catheter wherein multiple balloons are provided with a longitudinal configuration;

FIG. 8 is a radial cross section view taken along lines 8—8 of FIG. 7;

FIG. 9 is an axial cross section view taken along line 9—9 of FIG. 7;

FIG. 10 is a perspective view of the catheter illustrated in FIG. 3 further illustrating structures which can facilitate mixing and heat exchange;

FIG. 10A is a perspective view of an embodiment of the catheter having a distal end with a pigtail configuration;

FIG. 10B is a perspective view of the catheter illustrated in FIG. 10A with the distal end straightened by a stylet 174 to facilitate insertion of the catheter;

FIG. 28a is a top view schematic of a catheter having a semi-circularly shaped heat transfer element.

FIG. 28b is a side view of the catheter system illustrated in FIG. 28a

FIG. 28c is a front view of the catheter system illustrated in FIG. 28a

FIG. 29a is a top view schematic of a catheter having a loop shaped heat transfer element.

FIG. 29b is a side view of the catheter system illustrated in FIG. 29a

FIG. 29c is a front view of the catheter system illustrated in FIG. 29a

FIG. 30a is a top view schematic of a catheter having a figure-eight loop shaped heat transfer element.

FIG. 30b is a side view of the catheter system illustrated in FIG. 30a

FIG. 30c is a front view of the catheter system illustrated in FIG. 30a

FIG. 31 is a flow chart for treating cardiac arrest in a patient using the present invention.

FIG. 32 is a flow chart of the steps for cardiopulmonary resuscitation (CPR).

DETAILED DESCRIPTION OF THE PREFERRED EMBODIMENTS

Figure 1:
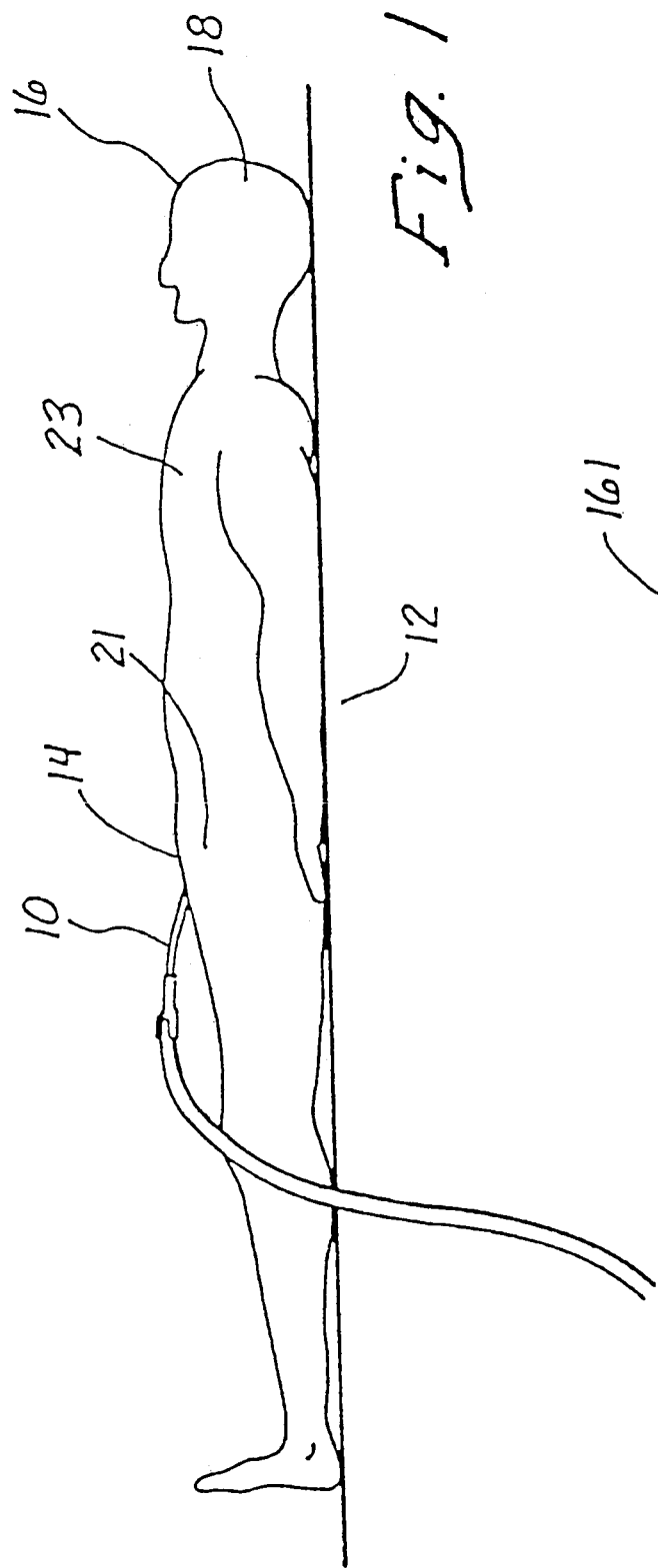
FIG. 1 is side elevation view of a patient lying in a prone position with a heat exchange catheter of the present invention appropriately inserted to facilitate hypothermic treatment of the patient's brain.
Figure 2:
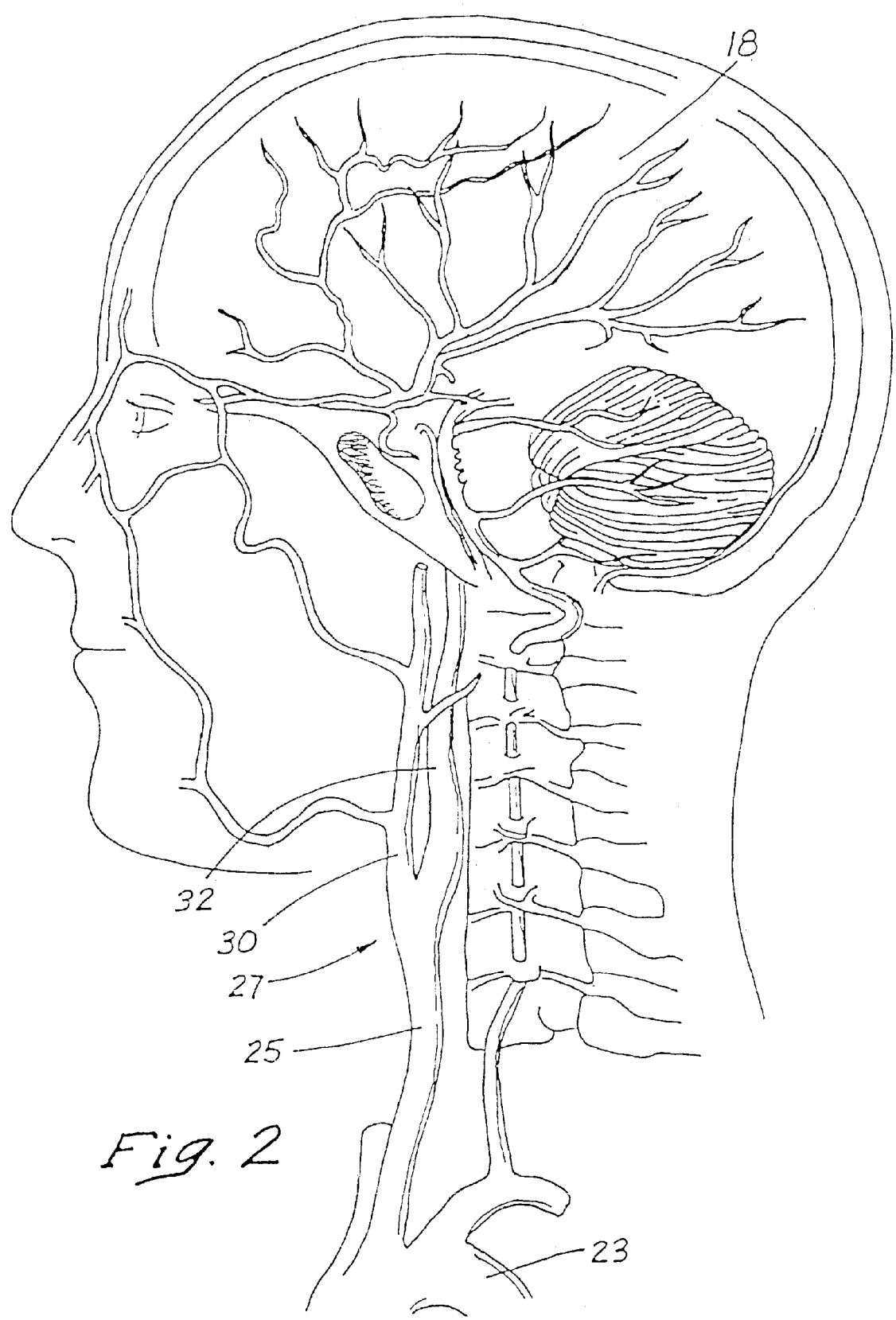
FIG. 2 is an enlarged side elevation view showing the vasculature associated with the patient's head and brain.

A heat exchange catheter is illustrated in FIG. 1 and designated generally by the reference numeral 10. The catheter 10 is operatively disposed with respect to a body 12 of a patient having a groin 14, a heat 16, and a brain 18. More specifically, the catheter 10 can be inserted percutaneously through a puncture or surgical cut down at the groin 14, and into the femoral artery 21. Following this initial introduction, the catheter 10 can be moved through the femoral artery 21 and the aortic arch 23, into the common carotid artery 25 best illustrated in FIG. 2. This common carotid artery 25 divides at a carotid branch 27 into an external carotid artery 30, which primarily supplies blood 31 to the face of the patient, and an internal carotid artery 32, which primarily supplies blood to the brain 18 of the patient.

In the concept of this invention, the brain 18 is merely representative of a portion of the body 12 of the patient, and the arteries 21, 25, 30 and 32 are merely representative of conduits which supply a body fluid, such as blood, to a selected portion of the body 12, such as the brain 18. By cooling the body fluid, such as blood 31, in the body conduit, such as the artery 32, the specific body portion, such as the brain 18, can be selectively cooled without significantly affecting the temperature of the remaining portions of the body 12.

Selective hypothermic treatment of the brain 18 is initially of particular interest as it captures the advantages of hypothermia during operative procedures associated with the brain 18 without also capturing the disadvantages of hypothermia with respect to other areas of the body 12. Thus, a surgeon operating to treat an aneurysm in the brain 18, for example, can initially cool the brain 18 in order to facilitate that procedure. This selective hypothermia will be particularly appreciated in those surgical procedures which are primarily directed to the brain 18. Procedures such as stroke, trauma, and other brain related injuries will also benefit up to and during from this selective hypothermia treatment.

Figure 3:
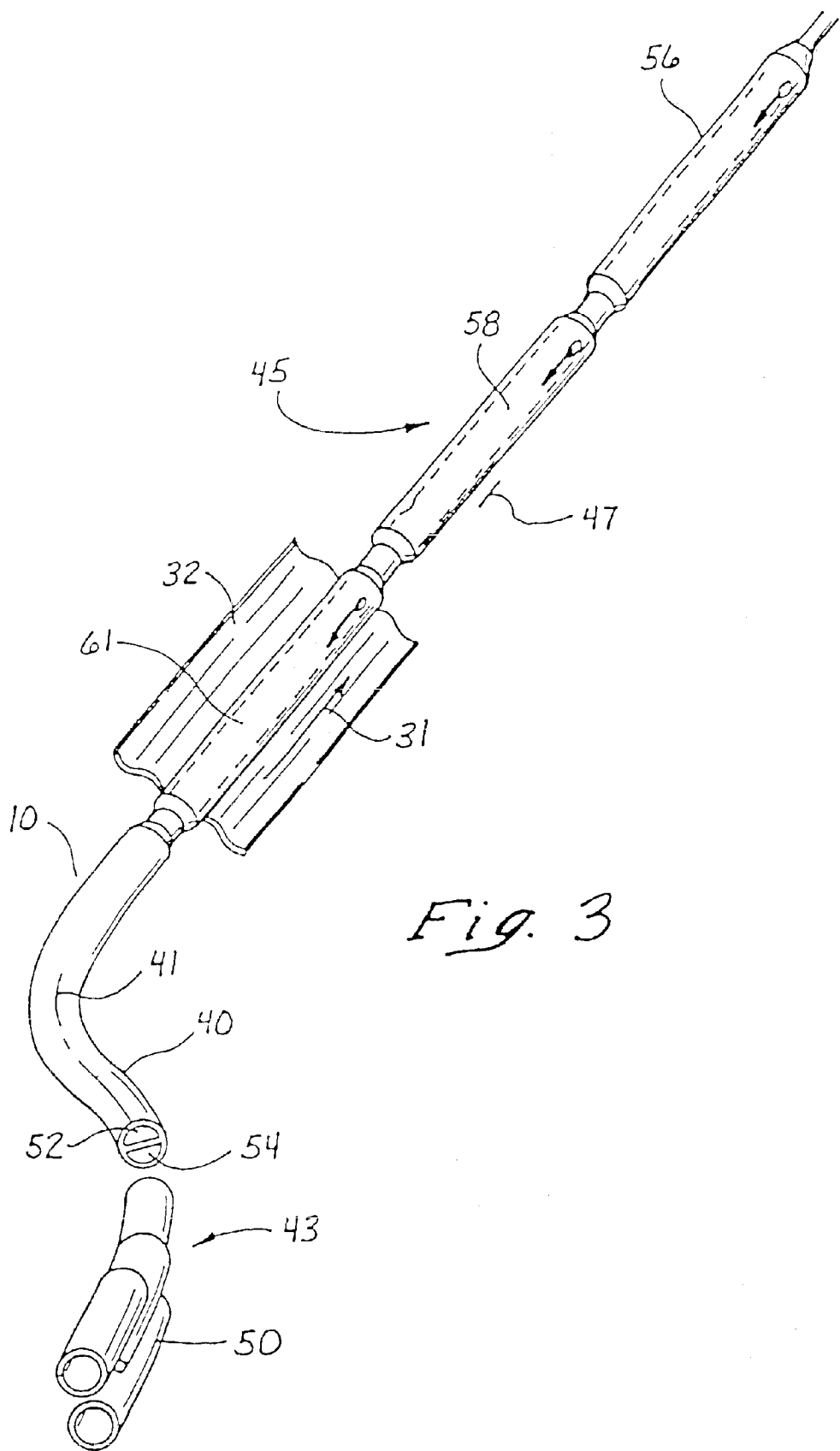
FIG. 3 is a perspective view partially in section of a heat exchange region of the catheter.

A preferred embodiment of the catheter 10 of the present invention is illustrated in FIGS. 3 and 4. From this perspective view, it can be seen that the catheter 10 includes a shaft 40 having an axis 41 which extends between a proximal end 43 and a distal end 45. When operatively disposed, a heat exchange region 47 at the distal end 45 is operatively disposed within the body 12, and a hub 50 at the proximal end 43 is disposed outside of the body 12. Within the shaft 40, a plurality of lumens 52 and 54 extend in fluid communication with the hub 50 and the heat exchange region 47.

A preferred embodiment of the heat exchange region 47 is illustrated in greater detail in FIG. 4 where three balloons 56, 58 and 61 are individually, separately and axially disposed along the shaft 40. It will be appreciated that although the illustrated embodiment includes three balloons, a single balloon or double balloon embodiment may offer further advantages in a particular procedure. All of the balloons 56, 58, and 61 are illustrated to have a significantly larger diameter than the shaft 40. This may not be the case in other embodiments. More specifically, it may be desirable to maximize the dimension of the shaft 40 in order to facilitate flow of the heat exchange fluid. This will also minimize the volume of fluid in the balloon and promote a more rapid heat exchange. In one such embodiment, the diameter of the shaft 40 is in a range between 50 and 90 percent of the diameter of the balloons 56, 58 and 61.

Each of the balloons 56, 58 and 61 can be formed from a piece of sheet material 62, 64 and 66 which is bound or otherwise fixed to the shaft 40 to form a cavity 63, 65 and 67, respectively. An inlet hole 70 provides fluid communication between the lumen 54 and the cavity 63 of the balloon 56. Similar inlet holes 72 and 74 are provided for the balloons 58 and 61. In a like manner, an outlet hole 76 can be formed in the wall of the shaft 40 to provide fluid communication between the lumen 52 and the cavity 63 of the balloon 56. Similar outlet holes 78 and 81 are provided for the balloons 58 and 61, respectively. With this structure, it can be seen that the lumen 54 functions primarily as an inlet lumen for a heat exchange fluid which is illustrated generally as a series of arrows designated by the reference numeral 85.

Initially, the heat exchange fluid 85 is introduced through the hub 50 (FIG. 3) and into the inlet lumen 54. From the lumen 54, the heat exchange fluid 85 passes through the inlet holes 70, 72, 74 and into the respective balloon cavity 63, 65, and 67. The heat exchange fluid 85 then passes into the outlet hole 76, 78, 81 and into the outlet lumen 52 and the hub 50 to regions exterior of the catheter 10.

After the heat exchange fluid 85 is remotely cooled, it is circulated through the balloon cavities 63, 65 and 67 to provide a cold temperature fluid on the inner surface of the sheet materials 62, 64 and 66 which form the walls of the balloons 56, 58 and 61, respectively. With a body fluid, such as blood 31, flowing exteriorly of the balloons 56, 58 and 61, heat transfer occurs across the sheet materials 62, 64 and 66, respectively.

It can be appreciated that this circulation of the heat exchange fluid 85 can be formed with any structure of the shaft 40 which provides two lumens, such as the lumens 52 and 54, each of which can have access to the balloon cavities, such as the cavities 63, 65 and 67. In one embodiment of the shaft 40 illustrated in FIG. 5, a septum 90 is provided which separates the cylindrical shaft 40 into two equally sized lumens 52 and 54. In the embodiment of FIG. 6, the cylindrical shaft 40 is provided with a cylindrical septum 92 which provides the lumen 54 with a circular cross section and the lumen 52 with a moon-shaped cross section. In such an embodiment, the lumen 54 must be defined off-axis from the shaft 40 in order to have access to the balloon cavities, such as the cavity 63.

One of the advantages of a multiple balloon embodiment of the catheter 10 is that the flow and temperature of the heat exchange fluid 85 can be more easily controlled along the entire length of the heat exchange region 47. Realizing that the heat exchange fluid 85 will be coolest prior to entering into a heat exchange with blood 31, and warmest after that heat exchange, one can advantageously control not only the velocity and volume of flow, but also the direction of the flow within each discrete balloons 56, 58 and 61. Another advantage of a multiple balloon design is the ability of the catheter to bend and flex when placed in a curved vasculature. Single balloon designs would be rigid, stiff and inflexible by comparison.

In order to facilitate the maximum heat exchange between the fluid 85 and the blood, it is desirable to provide a balanced flow of the heat exchange fluid 85 along the entire length of the heat exchange region 47. In the embodiment illustrated in FIG. 4, efficient heat transfer is facilitated by countercurrent flow where the heat exchange fluid 85 is directed to flow counter to the flow of the blood 31. To that end, the inlet holes 70, 72 and 74 are positioned distally of the outlet holes 76, 78 and 81, respectively. As the blood 31 flows distally along the outer surface of the catheter 10, this relative position of the inlet holes and outlet holes causes the heat exchange fluid to flow in the opposite direction, proximally in each of the balloons 56, 58 and 61.

The amount of flow within each of the balloons 56, 58 and 61 can also be controlled by the size of the inlet holes 70, 72, 74 and outlet holes 76, 78, and 81. In a preferred embodiment, this flow control is provided solely by the inlet holes 70, 72 and 74; the outlet holes 76, 78 and 81 are sized larger than their respective inlet holes so that they offer little resistance to flow. In this embodiment, the inlet holes 70, 72 and 74 are sized to be progressively smaller from the distal end 45 to the proximal end 43. Thus the hole 70 is larger than the hole 72 which is larger than the hole 74. As a result, the resistance to the flow of heat exchange fluid 85 in the most distal balloon 56 is less than that in the most proximal balloon 61. This ensures that the coolest heat exchange fluid 85 is shared equally among all of the balloons 56, 58 and 61 regardless of their position along the shaft 40. In an embodiment wherein the flow is controlled by the outlet holes 76, 78 and 81, these holes can also be provided with a relatively reduced size from the distal end 45 to the proximal end 43. With any of these structures, a more balanced flow of the heat exchange fluid can be achieved in order to facilitate the highest degree of heat exchange along the entire heat exchange region 47. Alternatively, the flow of heat exchange fluid can also be balanced by providing the holes 76, 78 and 81 with non-circular configurations. For example, these holes may be formed as longitudential slits extending axially of the catheter.

A further embodiment of the invention is illustrated in FIG. 7 wherein a single sheet of material 101 is used to form separate and distinct individual balloons, two of which are designated by the reference numerals 103 and 105. As opposed to the radial balloons 56, 58 and 61 of the previous embodiment, the balloons 103 and 105 extend axially along the surface of the shaft 40. For example, the balloons 103 and 105 form individual balloon cavities 107 and 110, respectively, which extend from a distal end 112 to a proximal end 114.

This embodiment of the catheter containing the axial balloons 103 and 105 may include a shaft 40 with a slightly different configuration. As best illustrated in FIG. 9, the shaft 40 may include an outer tube 121 having an outer surface to which the sheet material 101 is attached and within which is disposed a distal sealing plug 123. An inner tube 125, which can be disposed coaxially with the outer tube 121, has an inner lumen 127 and defines with the outer tube 121 an outer lumen 130. A pair of inlet holes 132 and 134 provide flow fluid communication between the inner lumen 127 and the balloon cavities 107 and 110, respectively. Similarly, a pair of outlet holes 136 and 138 provide fluid communication between the balloon cavities 107 and 110 and the outer lumen 130, respectively. An inner plug 141 disposed between the inner tube 125 and the outer tube 121 to seal the outer lumen 130 between the inlet holes 132, 134 and outlet holes 136, 138. For the reasons previously noted, a preferred embodiment has inlet holes 132, 134 which are disposed distally of and sized smaller than the outlet holes 136, 138, respectively. This orientation will provide countercurrent flow in a catheter 10 which is inserted downstream into an artery such as the carotid artery 25.

Embodiments which are intended to maximize heat transfer will take advantage of the fact that heat exchange is enhanced when either, or both, the body fluid or the heat exchange fluid is provided with well mixed flow. Mixing can be enhanced by providing irregular surfaces next to which either of these fluids flow. For example, with reference to FIG. 4, it will be noted that a spring 150 can be disposed around the shaft 40 inside each of the balloons, such as the balloon 61. In this embodiment, the spring 150 upsets the laminar flow of the heat exchange fluid 85 thereby producing the desired mixing of this fluid. Other structures can be positioned within the cavities formed by the balloons 56, 58 and 61.

Mixing can also be enhanced within the body fluid which flows along the outer surface of the catheter 10. In this case, the multiple radial balloon embodiment illustrated in FIG. 4 is of advantage as each of the balloons 56, 58 and 61 represents a peak and defines with the adjacent balloon a valley along which the blood 31 flows. This series of peaks and valleys also upsets the laminar flow of the body fluid. Mixing of the body fluid can also be enhanced by providing other structures along the outer surface of the sheet material 62, 64 and 66 which form the balloons as well as any exposed areas of the shaft 40 in the heat exchange region 47. By way of example, a multiplicity of granules 145 can be adhered to the outer surface of the radial balloons 56, 58 and 61 or the axial balloons 103 and 105 as illustrated in FIG. 9. Ridges can also be provided along these surfaces.

With some body fluids, it may be desirable to inhibit turbulent flow and facilitate laminar flow. This may be true for example in the case of blood where undesirable hemolysis may occur in response to increased turbulence. Such an embodiment might be particularly desirable for use with radial balloons where an outer balloon 152 would promote laminar flow by reducing the height differential between the peaks and valleys defined by the balloons 56, 58 and 61. This outer balloon 152 is best illustrated in FIG. 10. To further promote laminar flow, the outer surface of any structure in the heat exchange region 47 can be provided with a coating 154, such as a hydrophilic or a hydrophobic coating to modify the boundary layer. Thus the outer surface of the shaft 40 as well as the outer surface of any of the balloons 56, 58, 61, 103, 105 and 152 can be provided with the coating 154. The coating 154 may also include other ingredients providing the catheter 10 with additional advantageous properties. For example, the coating 154 may include an antithrombogenic ingredient such as heparin or aspirin. Such a coating 154 would not only inhibit platelet deposition but also the formation of blood clots.

As previously noted, the characteristics of the heat exchange fluid 85 may also be of importance in a particular heat exchange environment. Although the heat exchange fluid 85 may include various liquids, it is believed that gases may provide the greatest temperature differential with the body fluid. Particularly if this fluid includes blood, gases that are inert or otherwise compatible with the vascular system will be appreciated. Although several inert gases might fulfill these requirements, carbon dioxide is used for the heat exchange fluid 85 in a preferred embodiment of the invention.

A further embodiment of the catheter 10 is contemplated for maximizing the surface area available for heat exchange. As illustrated in FIGS. 10A and 10B, the catheter 10 can be formed with a distal end 45 of the shaft 40 disposed in the natural configuration of a spiral or pigtail 172. The relatively large diameter of the pigtail 172 facilitates heat exchange, but tends to deter from a low profile desire for insertion. Under these circumstances, it may be advantageous to insert the catheter 10 over a stylet or guidewire 174 in order to straighten the pigtail 172 as illustrated in FIG. 10B.

Figure 11:
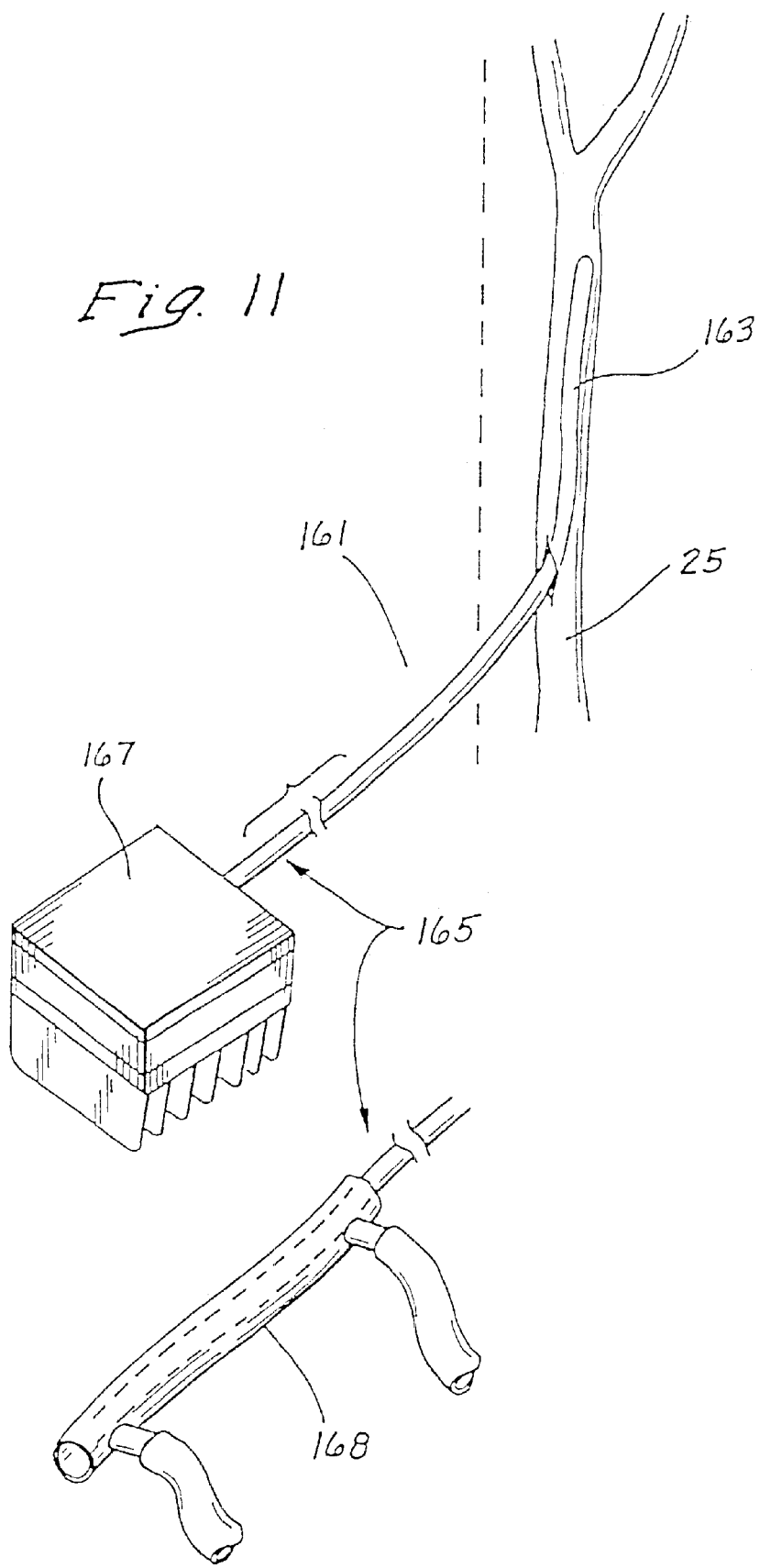
FIG. 11 is a schematic view of an embodiment including a heat pipe.

Hyperthermia and hypothermia for selective regions of the body can also be achieved by placing in the body conduit, such as the carotid artery 25, a heat pipe 161 best illustrated in the schematic view of FIG. 11. In this embodiment, the heat pipe 161 includes a distal end 163 and proximal end 165. The distal end 163 is adapted to be placed within the body conduit, such as the carotid artery 25. The proximal end 165 of the heat pipe 161 is adapted to be connected to an external heat sink or cooler, such as a thermoelectric cooler 167 or water jacket 168. A wick structure 170 is provided in the heat pipe 161 to facilitate a flow of heat exchange fluid from the cooler 167 to the distal end 163.

Figure 12:
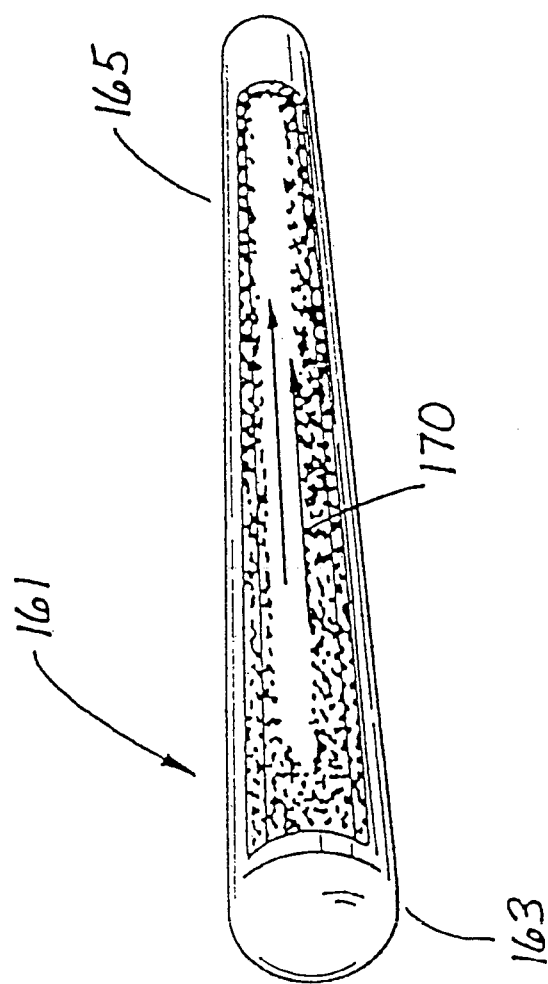
FIG. 12 is a schematic view, partially in section, of a heat pipe adapted for use in the embodiment of FIG. 11.

In a process involving the heat pipe 161, illustrated in FIG. 12, the heat exchange fluid is moved from the proximal end 165 of the heat pipe 161 either by gravity or by capillary action of the wick structure 170 to the distal end 163. At the distal end 163 of the heat pipe 161, heat is transferred from the body fluid, such as blood, to the heat exchange fluid in its liquid state. This heat exchange liquid absorbs a heat of vaporization as it passes into a vapor state in the heat pipe 161. The heat exchange fluid in its vapor state creates a pressure gradient between the ends 163 and 165 of the heat pipe 161. This pressure gradient causes the vapor to flow to the cooler 165 where it is condensed giving up its latent heat of vaporization. The heat exchange fluid in its liquid state then passes back through the heat pipe 161 through the wick structure 170 or by gravity. The passive heat exchange system provided by the heat pipe 161 is vacuum-tight and can be operated with a minimum amount of heat exchange fluid.

Figure 13:
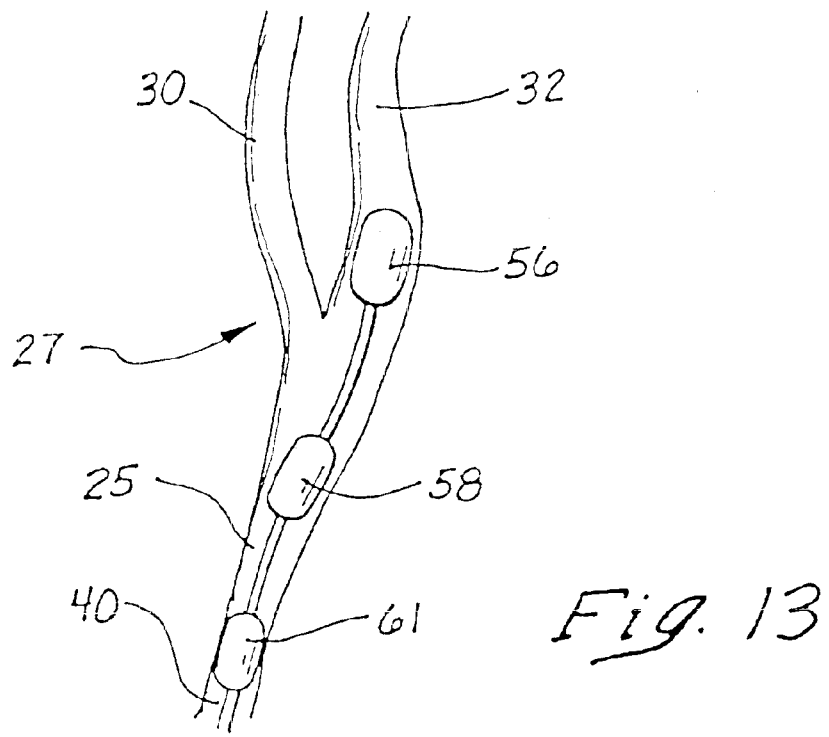
FIG. 13 is a top plan view of carotid artery branch illustrating one method of operation associated with the catheter.

Although the heat exchange catheter 10 will be advantageous in the hyperthermic or hypothermic treatment of any portion of the body 12, it is believed that it will be particularly appreciated in those procedures which can benefit from the hypothermic treatment of the brain 18, such as the treatment of ischemic stroke and/or head trauma. As previously noted in comments directed to FIG. 1, the catheter 10 can be inserted into the femoral artery in the groin 14 and directed through the aortic arch 23 into the common carotid artery 25. As illustrated in FIG. 13, the catheter 10 can then be moved into the region of the arterial branch 27 where it will encounter the external carotid artery 30 and the internal carotid artery 32. Since the external carotid artery 30 is directed primarily to the facial regions, it does not supply a significant amount of blood to the brain 18. In contrast, the internal carotid artery 32 is almost solely responsible for feeding the capillary bed of the brain 18. Based on these considerations, hypothermic treatment of the brain 18 is best addressed by cooling the blood in the internal carotid artery 32 without wasting any of the cooling properties on the external carotid artery 30. In a method associated with one embodiment of the invention, the most distal of the balloons, such as the balloon 56 in FIG. 13 is preferably positioned within the internal carotid artery 32. The more proximal balloons 58 and 61 can be disposed along the common carotid artery 25. This embodiment of the catheter 10 and its associated method will achieve a higher degree of heat transfer within the internal artery 32 than the external artery 30.

Figure 14:
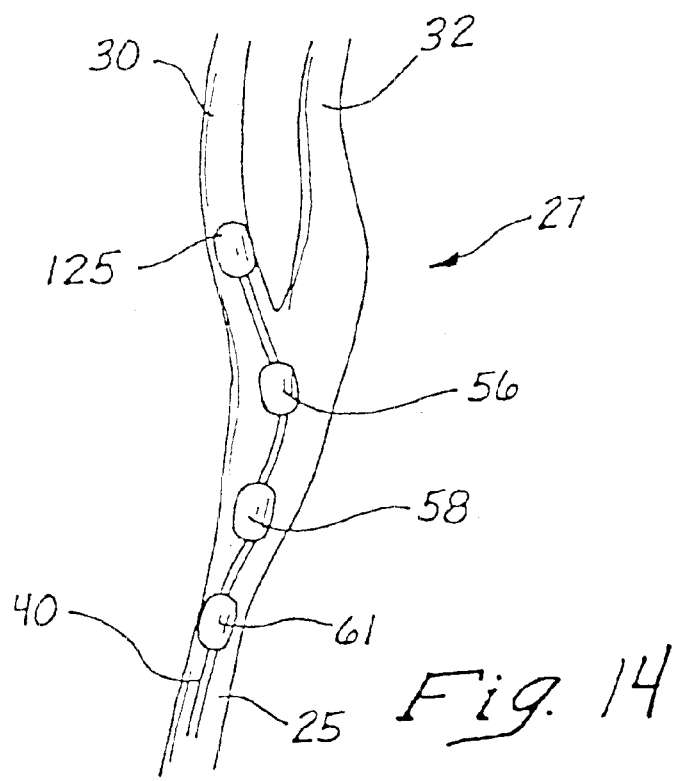
FIG. 14 is a top plan view similar to FIG. 13 and showing a further method of operation with the catheter.

In another embodiment of the catheter 10 best illustrated in FIG. 14, an occlusion balloon 175 is provided distally of the heat exchange region 47. In this embodiment, the occlusion balloon 175 will preferably be inflatable through a separate lumen in the shaft 40. As the catheter 10, approaches the carotid branch 27, the occlusion balloon 175 is directed into the external carotid artery 30 and inflated in order to at least partially occlude that artery. The remaining proximal balloons 56, 58 and 61 in the heat exchange region 47 are left within the common carotid artery 25 to promote heat exchange with the blood flowing to the branch 27. With the external artery 30 at least partially occluded, heat transfer occurs primarily with the blood flowing into the internal carotid artery 32.

Figures 15, 16:
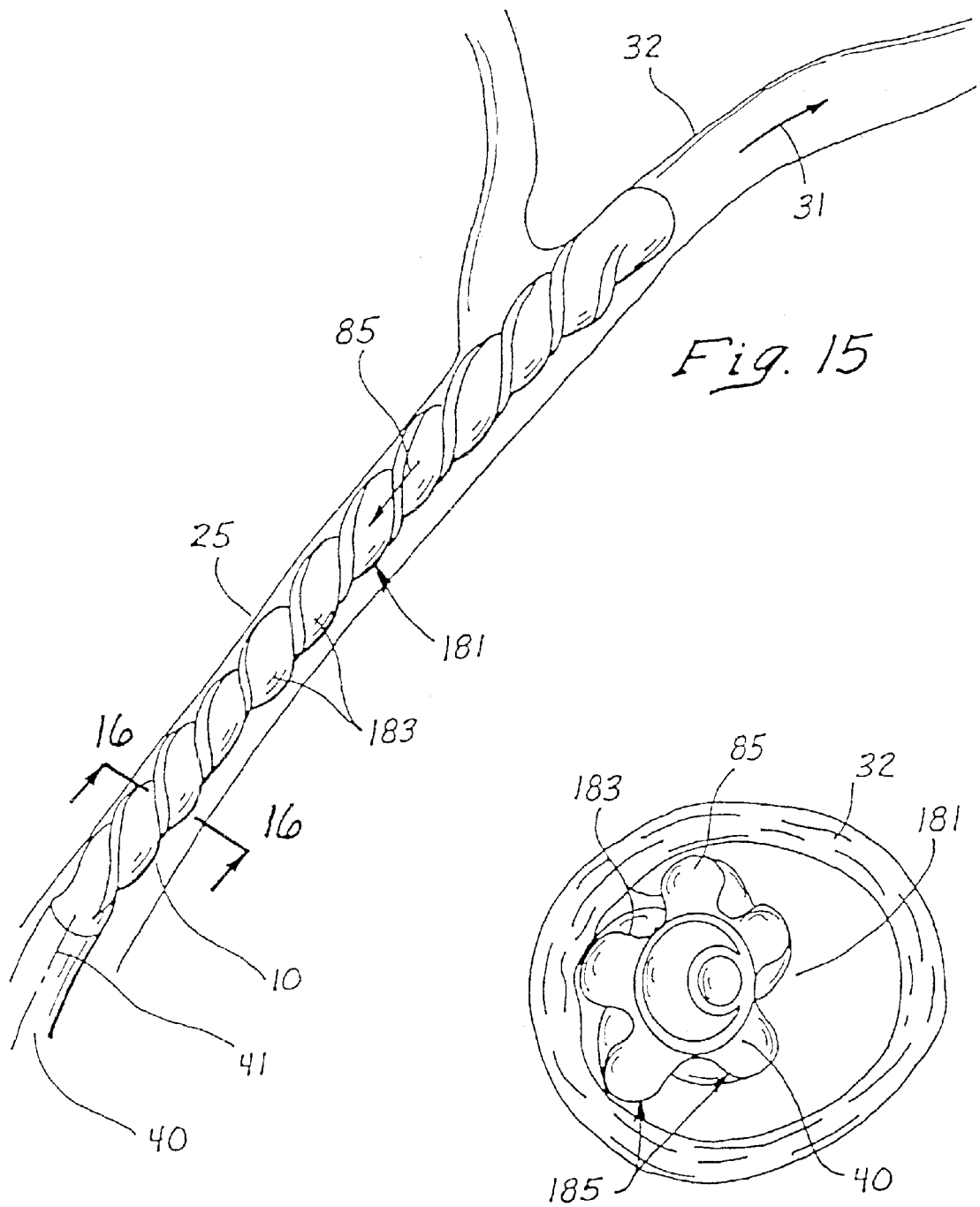
FIG. 15 is a top plan view of the carotid branch similar to FIG. 13 and showing a further method of operating a heat exchange catheter.
FIG. 16 is a radial cross section of the catheter taken along lines 16—16 of FIG. 15.

A further embodiment of the invention is illustrated in FIG. 15 operatively disposed in the common carotid artery 25 and internal carotid artery 32. In this case, the catheter 10 includes a balloon 181 which is attached to the distal end of the shaft 40. In this case the balloon 181 is provided with a spiral configuration. More specifically, the balloon 181 may be formed from several individual balloons, as with the embodiment of FIG. 7, for as individual flutes 183 on the single balloon 181. In either case, the separate balloons (such as the balloons 103, 105 of FIG. 7) or the flutes 183 are oriented in a spiral configuration around the axis 41 of the catheter 10. The shaft 40 can be provided with any of the configurations previously discussed such as the accentric configuration of FIG. 6.

By providing the balloon 181 with a spiral configuration, heat exchange is enhanced by at least two of the factors previously discussed. Notably, the surface area of contact is increased between the blood 31 flowing externally of the balloon 181 and the heat exchange fluid flowing internally of the balloon 181. The spiral configuration also enhances the mixing properties of both the blood 31 and the heat exchange fluid 85.

As noted, the heat exchange fluid 85 may be cooled to a sub-zero temperature such as −18° C. In order to thermally protect the internal lining of the artery 32 from direct contact with the sub-zero coolant, it may be desirable to provide the tips of the flutes 183 with a thicker wall 185, as shown in FIG. 16. This thicker wall 185 might be advantageous in any of the balloon configurations previously discussed, but would appear to be most advantageous in the embodiments of FIGS. 7 and 15 where the contact with the artery 32 tends to be more localized by the longitutudal balloons 103, 105 (FIG. 7) on the spiral flutes 183 (FIG. 15).

Figure 17:
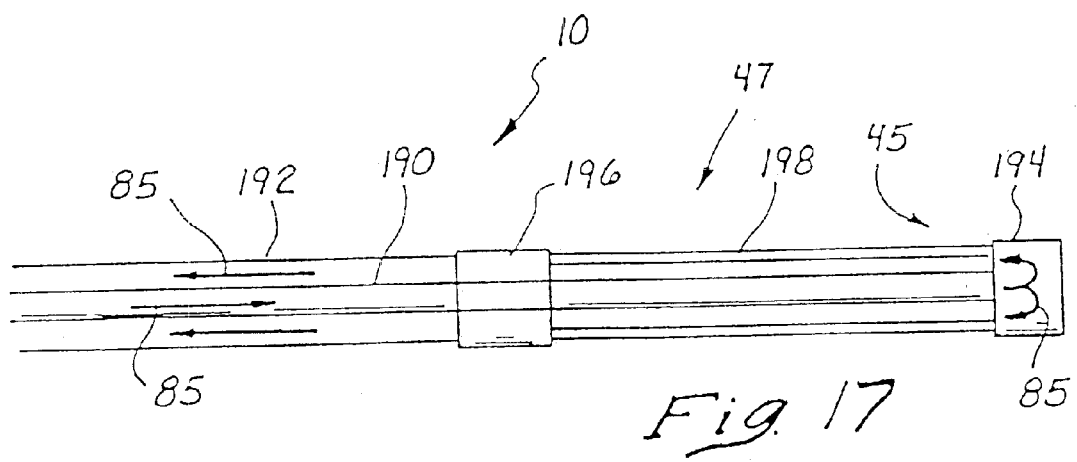
FIG. 17 is an axial cross section view of a further embodiment of the invention including hollow fibers in the heat exchange region.

Still a further embodiment of the invention is illustrated in FIG. 17. In this embodiment, the shaft 40 includes an inner tube 190 disposed within an outer tube 192. These tubes 190, 192 may be concentric and longitutingly movable relative to each other. The tubes 190, 192 terminate respectively in manifolds 194, 196. Between these manifolds 194, 196, a multiplicity of hollow fibers 198 can be disposed at the distal end 45 to define the heat exchange region 47 of the catheter 10. The hollow fibers 198 each include an internal lumen which provides fluid communication between the manifold 194 and 196. In operation, the heat exchange fluid 85 flows distally along the inner tube 190 into the distal manifold 194. From this manifold 194, the heat exchange fluid 85 flows into the internal lumens of the hollow fibers 198 proximally to the proximal manifold 196. The warmer heat exchange fluid 85 flows proximally from the manifold 196 between the inner tube 190 and the outer tube 192.

The hollow fibers 198 offer several advantages to this embodiment of the catheter 10. Notably, they provide a very high surface area between the blood 31 and the heat exchange fluid 85. This greatly enhances the heat exchange characteristics of this embodiment. Countercurrent flow can also be maintained further facilitating the heat exchange capabilities of this catheter.

Figure 18:
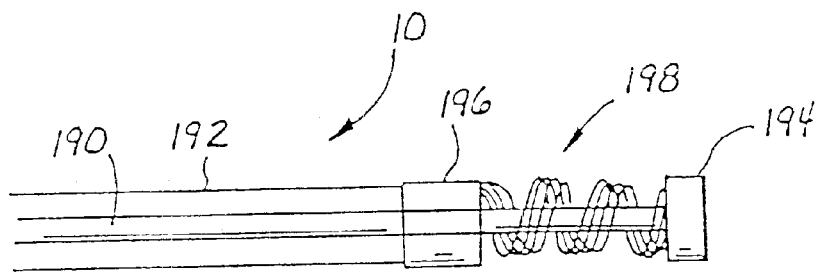
FIG. 18 is a side elevation view similar to FIG. 17 and illustrating the hollow fibers in a compacted configuration.
Figure 19:
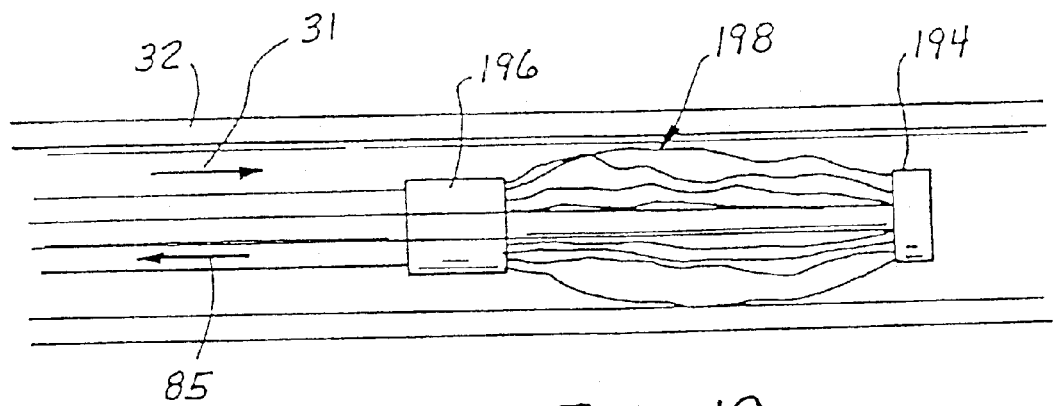
FIG. 19 is an axial cross section view of the catheter of FIG. 17 operatively disposed and configured to permit the hollow fibers to float and undulate within a blood stream.

The hollow fibers 198 can be spiraled as illustrated in FIG. 18 by twisting the inner tube 190 with respect to the outer tube 192. This characteristic can be used to provide a shorter and lower profile heat exchange region 47 in order to facilitate introduction of the catheter 10. A lower profile may also be obtained by separating the manifolds 194 and 197 a distance substantially equal to the length of the fibers 198. This will tend to hold the fibers in a straight, parallel relationship and thereby facilitate introduction of the catheter 10. The spiraled configuration of the hollow fibers 198 can be maintained during heat exchange in order to further increase the heat exchange area per unit length of the catheter 10. Alternatively, the fibers 198 can be positioned to loosely float and undulate between the manifolds 194 and 196 as illustrated in FIG. 19. This characteristic of the fibers 198 will not only provide the increased heat exchange area desired, but also promote mixing within the blood 31.

Generally speaking with respect to any of the balloon embodiments previously discussed, it will be appreciated that the advantages of this invention can be derived with respect to a single balloon. On the other hand, there seem to be several advantages associated with multiple balloon embodiments. Notably, a more even and balanced transfer of heat exchange can be achieved with multiple balloons. In addition, there appears to be better mixing with respect to both the blood 31 as well as the heat exchange fluid 85. Multiple balloons also provide an increased surface area relative to single balloon embodiments. Furthermore, the overall flexibility of the catheter 10 is enhanced with multiple balloons separated by interruptions which provide natural flex points for the catheter. When the balloons experience the high perfusion pressure, they become more stiff. The reduced diameter interruptions provide for increased flexibility at these joints.

Additionally flexibility can be derived by providing the shaft 40 with variable stiffness. This variability can be produced by different materials forming the shaft 40 along its length or alternatively, tapering or otherwise varying the diameter of the shaft 40. For example, the shaft 40 can be progressively tampered from its proximal end 43 to its distal end 45 in order to provide a softer and more flexible heat exchange region 47.

Figure 20:
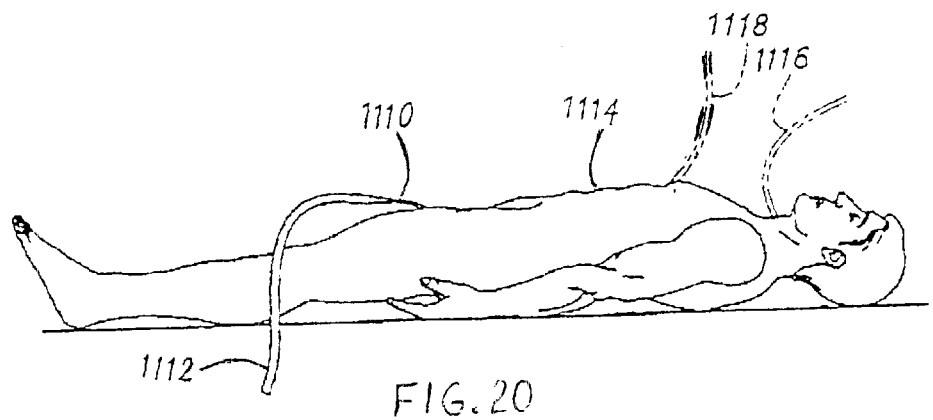
FIG. 20 is a side elevation view of a patient lying in a prone position with a heat exchange catheter in place in the groin. Placements in the chest and neck are shown in phantom.

Turning in detail to the drawings, FIG. 20 illustrates advantageous employment of heat transfer catheters in a body. The catheter 1110 is prepared and inserted into a body conduit. This insertion 1112 may be into the groin of the body 1114 as illustrated in full in FIG. 20. Shown in phantom are alternate locations for insertion in the neck 1116 and the chest 1118. Associate equipment including a heater/chiller, temperature signal monitors and monitors of other body functions, and drug sources supply the catheter independently of its location.

Figure 21:
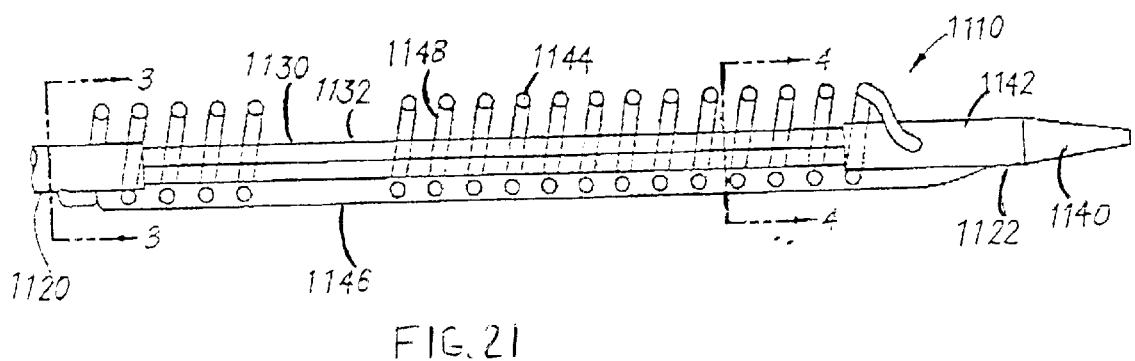
FIG. 21 is a side view schematic of a catheter having a helical heat transfer element.
Figure 22:
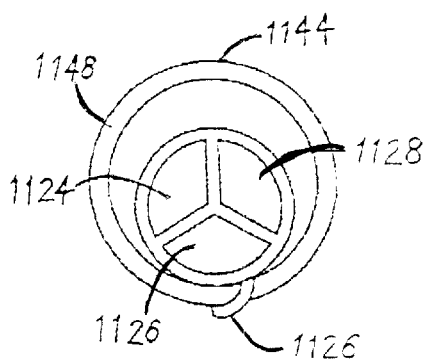
FIG. 22 is a cross-sectional view taken along line 3—3 of FIG. 21.
Figure 23:
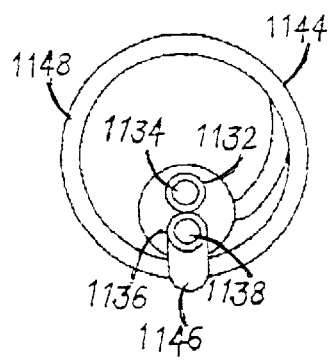
FIG. 23 is a cross-sectional view taken along line 4—4 of FIG. 21.

FIG. 21 illustrates a catheter, generally designated 1110, which includes a shaft 1120. The shaft 1120 is flexible and yet allows entry into body conduits in a conventional fashion. There is a tapered head 1122 at the distal end of the shaft 1120 for ease of insertion. A hub (illustrated in the embodiment of FIG. 24), preferably with standard fittings for coupling with sources of pressurized heated or cooled fluid and returns, is arranged at the proximal end of the catheter 1110. In the embodiment of FIGS. 21 through 23, the cross-section of the shaft 1120 is shown to be divided into three lumens. A first lumen 1124 may provide input. A second lumen 1126 may provide output and a third lumen 1128 may extend fully to the end of the head 1122 to provide infusion of medication and also receive a wire guide to assist in placement. Any number of septum configurations and numbers of lumens may be employed for the shaft 1120. The wall flexibility of the shaft 1120 is able to provide for substantial accommodation of associated elongate elements in fluid communication which may be inserted into the end thereof. Advantageously, the elongate elements are of the same overall cross-section as the associated lumen 1124, 1126, 1128 such that the element may fit directly into the lumen.

An elongate body, generally designated 1130, extends from the shaft 1120 to the head 1122. This elongate body 1130 is illustrated in this first embodiment to be an input tube 1132 including an fourth, input lumen 1134 in fluid communication with the first, input lumen 1124. The elongate body 30 further includes an infusion tube 1136 having a fifth, infusion lumen 1138 extending therethrough. These tubes 1132 and 1136 are a bit more rigid than the shaft 1120. Alternately, the shaft 1120 may extend to the head 1122 to provide the same function. The head 1122 may include a frusto-conical end portion 1140 and a cylindrical portion 1142. The cylindrical portion 1142 may in fact be a small section of the same tubing defining the shaft 1120. The frusto-conical end portion 1140 may also be of resilient material but includes a single passageway therethrough, exiting at the apex end of the cone. The infusion tube 1136 is in flow communication with the passage through the frusto-conical end portion 1140.

An elongate element 1144 is arranged in a helical configuration extending axially along the elongate body. This element 1144 is in communication with the second, output lumen 1126 at the shaft 1120. At the cylindrical portion 1142 of the head 1122, the elongate element 1144 is in fluid communication with the fourth, input lumen 1134 within the tube 1132. To maintain the helical arrangement of the elongate element 1144, a bonding material 1146 runs the length of the elongate body 1130 encapsulating a small fraction of the length of each turn 1148 of the elongate element 1144. The elongate element 1144 terminates in the cylindrical portion 1142 of the head 1122 and in communication with the input tube 1132. As can be seen from FIG. 21, the pitch of each of the turns 1148 is substantially shorter than the lengths of the elongate element 1144 of each turn 1148. As such, the hoop area of the turn 1144 is substantially larger than the cross-section of the body 1130 extending through that hoop area. Consequently, there is the prospect of body fluid flow between the elongate body 1130 and the principal length of the turns 1148.

The elongate element 1144 is of thin-walled and collapsible material employed for making catheter balloons. The nature of the elongate element 1144 is that the heat transfer lumen extending therethrough is not appreciably expanded throughout the portion of the elongate element forming the helical configuration.

In operation, a wire guide (not shown) may be extended through the third lumen 1128 of the shaft 1120, the infusion tube 1136 and the head 1122. Once guided into position, the wire guide is withdrawn and the infusion tube 1136 may be used for medication. Heating or cooling fluid may then be introduced through the first lumen 1124, the input tube 1132 and the cylindrical portion 1142 to the heat transfer lumen of the elongate element 1144. The introduction of fluid to the element 1144 is at the distal end of the catheter with the flow through the element 1144 being toward the proximal end of the catheter, to be carried away from the heat transfer area by the second, output lumen 1126. Sufficient pressure is introduced with the heating or cooling flow so as to expand the elongate element 1144 away from the body 1130. This element 1144 is a thin walled tube and without pressure is collapsible under fluid pressure of the body fluid. Once the heating and/or cooling operations have taken place, a vacuum may be drawn on the cooling circuit to further retract the turns 1148 toward the body 1130. When elongate element 1144 is expanded by the working fluid, the body fluid is free to flow between the helical elongate element 1144 and the elongate body 1130.

Figure 24:
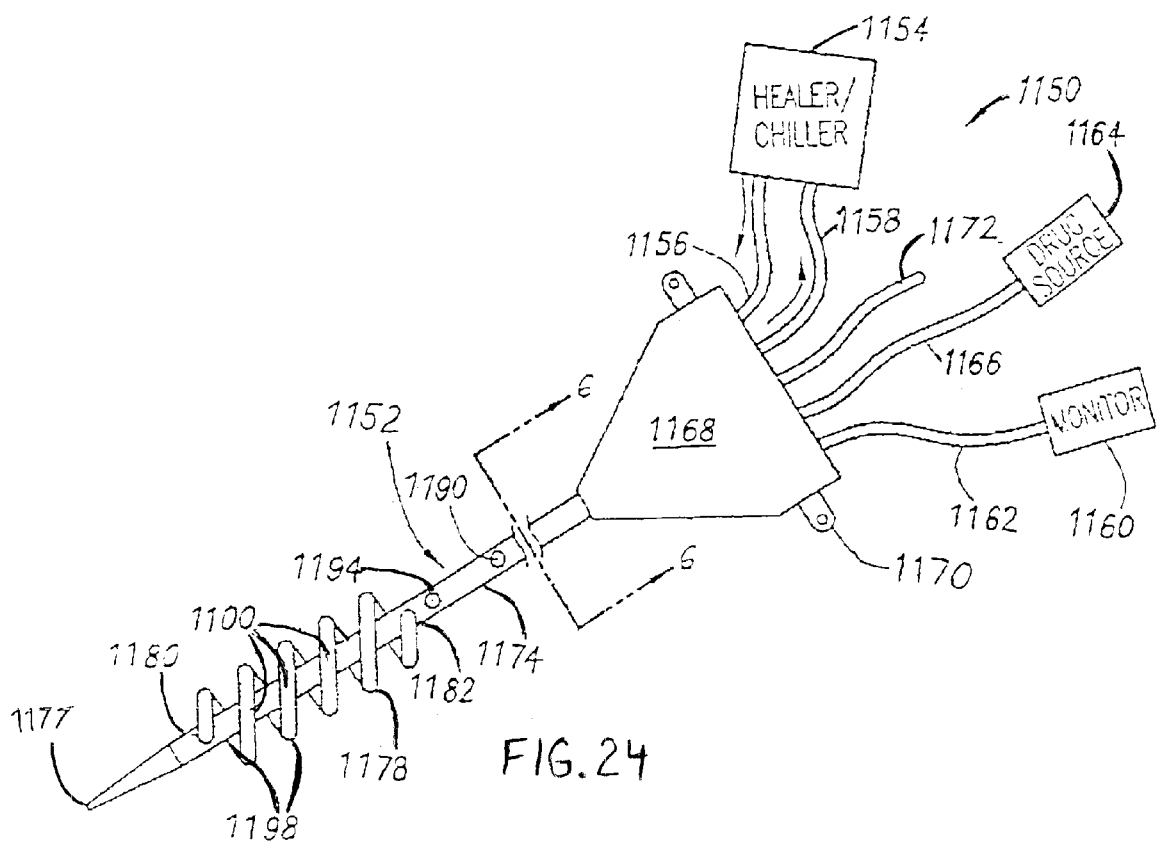
FIG. 24 is a side view of a catheter system.
Figure 25:
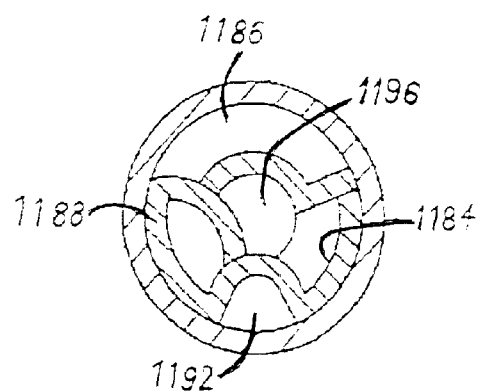
FIG. 25 is a cross-sectional view taken along line 6—6 of FIG. 24.

A second embodiment is illustrated in FIGS. 24 and 25 with functions and construction applicable to each disclosed embodiment. A system, generally designated 1150, is shown for managing and otherwise controlling patient temperature while providing access to the central venous system of a patient. As shown, beginning at the proximal side of the system 1150, the system 1150 includes a central venous access and heat exchange catheter 1152 that receives a heat exchange fluid, or working fluid, from a heater/chiller 1154, with the fluid circulating in a closed loop. The fluid preferably is saline, but other fluids such as refrigerant can be used. Either the fluid flow rate and/or the temperature of the fluid is controlled by a controller associated with the heater/chiller 1154 based on a patient temperature feedback signal to control the amount and, if desired, the rate at which heat is added or subtracted from the patient. The controller can be implemented by a software-executing processor or by discrete logic circuits or other electronic circuitry to establish a desired patient temperature by appropriate controlling the flow rate and/or heat exchanger in response to a temperature signal derived from a sensor in the patient. In any case, working fluid is supplied from the heater/chiller 1154 via a working fluid supply line 1156, and working fluid returns to the heater/chiller 1154 via a working fluid return line 1158.

As also shown in FIG. 24, at least two central venous components can be in communication with the catheter 1152 for undertaking central venous functions in addition to controlling the temperature of the patient. These functions include and are not limited to drug infusion and blood extraction for blood monitoring, as well as blood pressure monitoring. For instance, a blood monitor 1160 can communicate with the catheter 1152 via a line 1162 to monitor blood pressure or withdraw blood from the central venous system of the patient. Also, a drug source such as a syringe 1164 can engage the catheter 1152 via a connector with line 1166 for infusing drugs or other medicament such as epinephrine into the patient. The components 1154, 1160 and 1164 can all be connected to the catheter 1152 via a proximal connector hub 1168 of the catheter 1152. The hub 1168 can be formed with a suture anchor 1170 or other anchor structure such as tape for providing a means to fasten the catheter 1152 to the skin of the patient for long-term use. Also, a guide wire lumen tube 1172 may be engaged with the hub 1168 and extend therethrough to a guidewire lumen.

Turning to the portion of the system 1150 distal to the hub 1168, a preferably plastic, flexible catheter elongate body 1174 extends distally away from the hub 1168. The body 1174 is biocompatible, and can be coated with an antimicrobial agent and with an anti-clotting agent such as heparin. The body 1174 can be a unitary piece of hollow plastic or it can be made of more than one coaxial tube. Distally bonded to a portion or the body 1174 is a comparatively more rigid frusto-conical shaped guide head 1176, an open distal end of which can establish a distal infusion port 1177.

A flexible, collapsible, helical-shaped heat exchange elongate element 1178 surrounds the body 1174. The heat exchange element 1136 can be made of a plurality of discrete turns that are formed separately from each other and then joined together to communicate with each other. However, in a more preferred embodiment more easily fabricated, the elongate element 1178 is a single, unitary tube made of very thin catheter balloon material that extends from a first end 1180 to a second end 1182 and the element 1178 includes a heat transfer lumen extending longitudinally therethrough. The heat transfer lumen is in fluid communication with an input lumen 1184 which is in turn in communication with the supply line 1156. The heat transfer lumen of the element 1178 is also in communication at the second end 1182 with an output lumen 1186 communicating with the return line 1158. The elongate element 1178 is in communication with the output lumen 1186 at the second end 1182. Thus, working fluid flows distally through the input lumen 1184, into the helical transfer lumen of the elongate element 1178, and then proximally back through the element 1178 and the output lumen 1186. In another embodiment, the working fluid flows proximally through the input lumen 1184, into the helical transfer lumen of the elongate element 1178, and then distally back through the element 1178 and the output lumen 1186.

In addition to the input lumen 1184 and output lumen 1186, the catheter 1174 may have two or more infusion lumens which may be operated simultaneously with the control of the patient's temperature. Specifically, the first infusion lumen 1188 terminates at a medial outlet port 90 and a second infusion lumen 1192 terminates at a separate outlet port 1194. Both lumens 1188 and 1192 are separated from the heat transfer fluid and both extend to the hub 1168. A guide wire tube 1196 communicates with the tube 1172 extends to the distal port 1178. These several passages provide communication for the introduction of medicine, the sampling of blood, the sensing of temperature and other purposes requiring access into the body passageway. The ports are shown separated to preclude mixing of drugs in the blood stream. The ports may also provide for the sampling of blood, the sensing of temperature and other purposes requiring access into the body passageway.

Looking specifically to the elongate element 1178, a plurality of turns 1198 are shown to define the helix which extends longitudinally of the elongate body 1174. The turns 1198 are bonded along a fraction of the length of each turn at locations 1100 and are otherwise displaced from the body 1174. This allows body fluid flow between the turns 1198 and the body 1174. Again, the turns 1198 are of thin-walled, flexible material. The material need only retain the working fluid and may collapse under fluid pressure of the body fluid when the heat transfer lumen is at atmospheric pressure. Even through the term "balloon" is used, the material is not capable of substantial stretching.

The catheter 1150 is advanced (possibly through an introducer sheath) into the vena cava of the patient through a groin entry point (1112 in FIG. 20), through a neck entry point (1116 in FIG. 20) or through a chest entry point (1118 in FIG. 20) to the central venous system of the patient. When advanced through the groin, the cathether is advanced through the femoral vein to the iliac vein and then to the inferior vena cava. When advanced through the neck, it is passed into the jugular vein. When advanced through the chest, it is directed into the subclavian vein to the superior vena cava. Working fluid is then circulated through the input lumen 1184. This fluid inflates the elongate element 1178 and causes it to be distanced from the catheter body 1152 except at the bond points 1100. The body fluid then is able to flow around all surfaces of each turn 1198 to promote efficient heat transfer. To withdraw the catheter from the patient, the catheter may be uncoupled from the heater/chiller 1154 and the catheter pulled proximally from the patient. The element 1178 is allowed to collapse and further collapses as the catheter is drawn through the restricted entry point.

Figure 26:
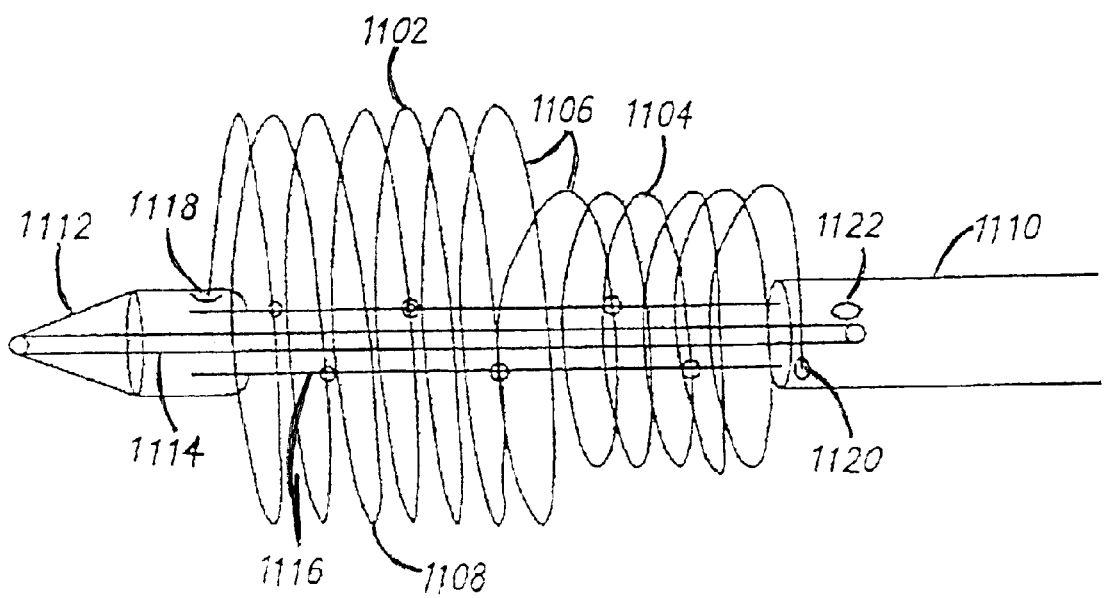
FIG. 26 is a schematic layout of another catheter having a helical heat transfer element.
Figure 27:
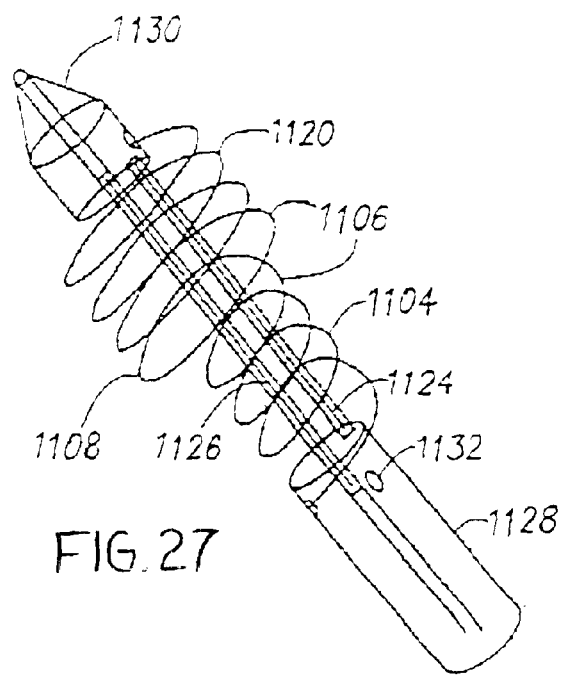
FIG. 27 is yet another schematic layout of another catheter having a helical heat transfer element.

Two further embodiments are illustrated in FIGS. 26 and 27. These embodiments do not require full discussion of each component as they employ the same concepts as already discussed. The format is somewhat amended. First, both embodiments feature two sets 1102 and 1104 of turns 1106 of an elongate element 1108. The sets 1102, 1104 encounter different diameters in the flow string. Alternatively, the turns are separately supplied by separate input lumens with either separate output lumens or a common output lumen for both.

In the embodiment of FIG. 26, the catheter body 1110 includes four lumens, an input lumen, and output lumen, a wire guide lumen and an infusion lumen. The body 110 may extend fully to the conical head 1112 or terminate at the end of the helix. In the latter case, tubes are associated with each of the lumens as needed to extend flow communication to the head 1112. The guide wire lumen extends via a tube 1114 to the head 1112. The input lumen extends via a tube 1116 to a base of the head 1112 where there is an attachment 1118 to the element 1108. An attachment 1120 is provided between the other end of the elongate element 1108 and the output lumen within the body 1110. The infusion lumen of the body 1110 may include an infusion port 1122. As in the prior embodiments, the turns 1106 of the elongate element 1108 are preferably bonded at a bond point to one of the tubes 1114, 1116 to achieve appropriate spacing when deployed.

FIG. 27 illustrates a configuration where there are two distinct tubes 1124 and 1126 extending from the catheter body 1128. The tube 1124 is an input tube while the tube 1126 is a guide wire tube. Both extend to the head 1130. Again, an infusion port 1132 may be associated with an additional lumen. The fewer number of turns 1106 over that of the embodiment of FIG. 26 is simply indicative of empirical considerations dependent upon the length of the element 1108, the pressure and speed of flow through the element 1108 and the relative proportions of the components which enhance body fluid flow past the turns 1106.

The foregoing designs contemplate a maximum outside diameter for the expanded turns of the elongate element which is at about 1180 percent of the minimum inside diameter of the portion of the vein where the heat exchange component of the catheter is to be located. By using 1180 percent, there remains an annular area having a thickness of about 1110 percent of the vein diameter for flow. Clearly some part of the flow will then pass through within the turns to achieve maximum contact with the surface area and appropriate heat transfer.

Two further embodiments are illustrated in FIGS. 28a and 29a. These embodiments do not require full discussion of each component as they employ the same concepts as already discussed. Instead, only differences will be pointed out. In the embodiment shown in FIG. 28a, the catheter 1200 includes a shaft 1210 and an elongated element 1220 arranged in a semi-circle configuration around the catheter body 1230 as illustrated in FIG. 28c. FIG. 28b is a side view of the catheter 1200 in FIG. 28a. In the embodiment shown in FIG. 29a, the catheter 1300 includes a shaft 1310 and an elongated element 1320 arranged in loop configurations around the catheter body 1330 as illustrated in FIG. 29c. FIG. 29b is a side view of the catheter 1300 in FIG. 29a. FIGS. 30a, 30b and 30c illustrate yet another embodiment of a catheter 1400 with an elongated element 1420 arranged in figure-eight loop configurations around the catheter body 1430.

The process of the present invention can be appreciated in reference to FIG. 31. Commencing at block 546, basic life support algorithms are undertaken on a patient suffering from cardiac arrest. The basic life support activities can include one or more of the cardiopulmonary resuscitation (CPR) acts discussed below in reference to FIG. 32.

At block 548, in an attempt to quickly start the patient's heart beating again, particularly in the absence of a defibrillator, a precordial thump can be administered to the patient's chest. In addition, or if and when the defibrillator system 538 becomes available, at block 550 the defibrillator is engaged with the patient and the patient is defibrillated to start the patient's heart beating.

After initial defibrillation, the patient's heart rhythm is assessed at block 552. At decision diamond 554 it is determined in accordance with cardiac arrest resuscitation standards whether the patient exhibits ventricular fibrillation (VF) or ventricular tachycardia (VT). VF is defined as a pulseless, chaotic, disorganized rhythm characterized by an undulating irregular pattern that varies in size and shape with a ventricular waveform greater than 150 beats per minute. If no VF/VT is detected, indicating that the patient's heart is beating normally, some or all of the CPR acts shown in FIG. 32 are administered as necessary at block 556 for, e.g., up to three minutes.

If, on the other hand, it is determined at decision diamond 556 that the patient exhibits VF/VT, the patient is defibrillated up to, e.g., three times at block 558. In one preferred embodiment, defibrillation energy levels are 200 J (2 J/kg) for the first shock, 200 J–300 J (2–4 J/kg) for the second shock, and 360 J (4 J/kg) for the third and subsequent shocks (weight-based dosages are pediatric recommendations). CPR is then administered at block 560 for up to, e.g., one minute.

In accordance with the present invention, after defibrillation and CPR, moderate hypothermia is induced in the patient at block 562 to alleviate the results of global ischemia arising from cardiac arrest. It is to be understood that the step shown at block 562 can be undertaken at other convenient times including before defibrillation and CPR or concurrently therewith. In any case, the patient's temperature is lowered below normal body temperature, and as low as 32° C., by advancing one or both of the catheters 10, 1110 into the patient and then circulating coolant through the catheter 10, 1110.

In one embodiment of the present method, the first catheter 1110 is initially advanced into the vena cava through the groin to cool the patient while resuscitation personnel require access to the neck for intubation and for establishing rapid IV access. When CPR is complete, the second catheter 10 can be advanced into the vena cava through the relatively less septic neck, and if desired the first catheter 1110 can be removed from the relatively more septic groin area. It is to be understood that while this is one preferred sequence of the order of steps for inducing hypothermia in a cardiac arrest patient, other sequences can be used. For example, the first catheter 1110 can be used exclusively to the second catheter 10, the second catheter 10 can be used exclusively to the first catheter 1110, or both catheters 10, 1110 can be used together simultaneously.

FIG. 32 shows that CPR can include but need not be limited to checking defibrillator electrode/paddle engagement on the patient at block 564. Also, CPR can include establishing endotracheal access with the ET tube 544 at block 566 and then ventilating the patient using the ventilation system 542. If tracheal intubation is not possible, a laryngeal mask airway or Combitube can be used as alternatives.

Moreover, at block 568 intravenous (IV) access can be established using one of the catheters 10, 1110 or another catheter such as a Swan-Ganz catheter, and then cardiac arrest drugs such as epinephrine can be administered. If IV access is not attainable, epinephrine can be administered via the ET tube 544 using at least twice the intravascular dosage of at least 1 mg (0.01 mg/kg) every 3 minutes.

At block 570 other drugs can be considered for administration including buffers, antiarrhythmics, and atropine, and the installation of a pacemaker can also be undertaken. Any causes that can be corrected (such as, e.g., blocked airways) are corrected at block 572.

Figure 33:
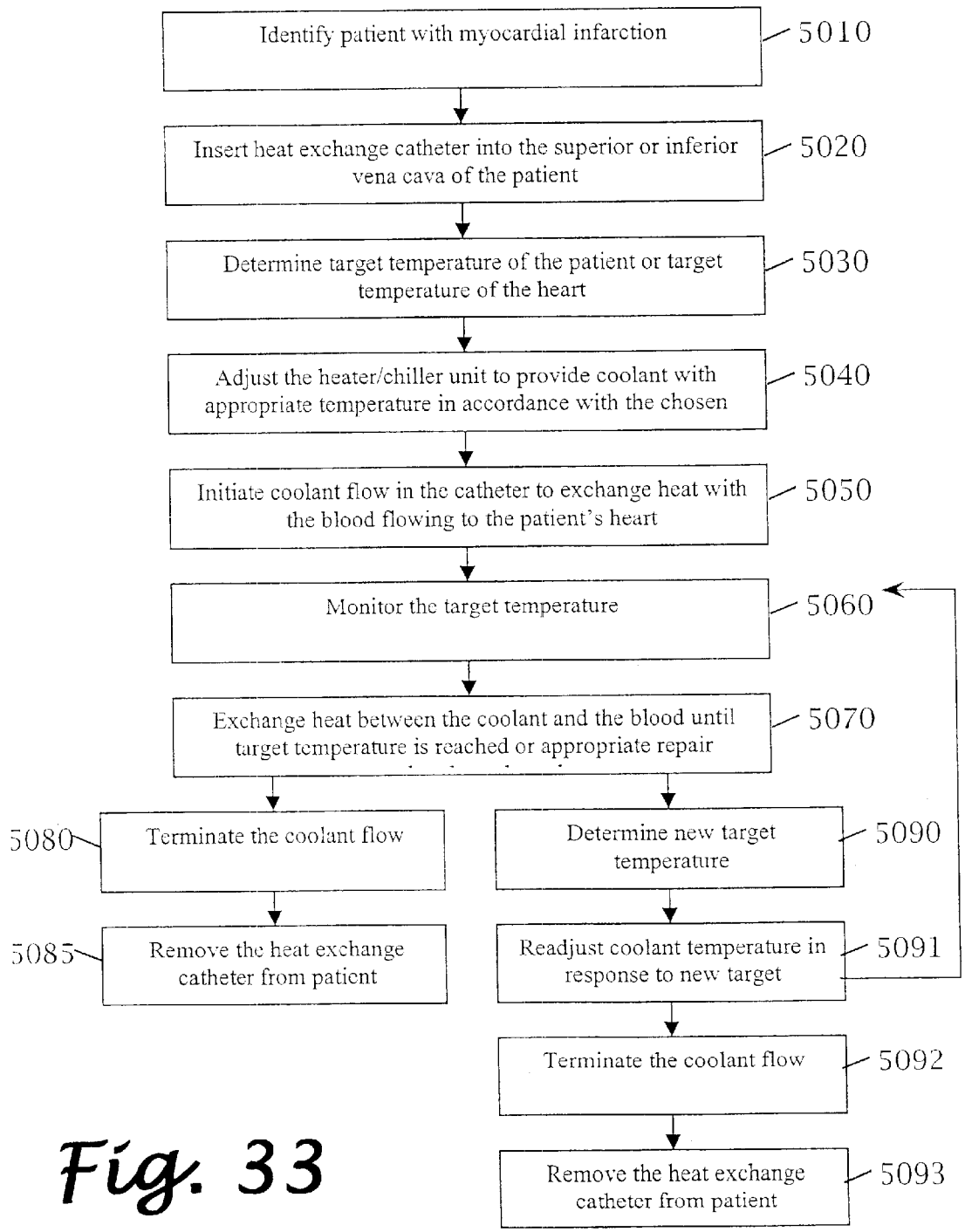
FIG. 33 is a flow chart of the steps for treating a patient with myocardial infarction.

FIG. 33 is a flow chart illustrating the use of an intravascular catheter to induce hypothermia of the heart to treat myocardial infarction. In step 5010, a patient with myocardial infarction is identified. In step 5020, a heat exchange catheter is inserted into the patient for placement in the superior or inferior vena cava. In step 5030, a target temperature is determined. The target temperature can be measured at many locations of the patient's body, including but not limited to, the heart, the bladder, the esophagus, the ear or the anus using a temperature sensor 1111. In step 5040, the heater/chiller unit 1154 controls the temperature of the coolant in accordance with the set target temperature. In step 5050, the coolant flows through the catheter's heat exchange element to enable the exchange of heat with the blood flowing into the heart of the patient. In step 5060, the target temperature is monitored. In step 5070, heat exchange takes place and the temperature of the patient is being modified. Once the target temperature is reached, the coolant flow may be terminated as in step 5080 and the heat exchange catheter removed from the patient as in step 5085. In the alternative, a new target temperature may be set as in step 5090, and the steps 5060 and 5070 may be repeated. Additionally, once the new target temperature is reached, step 5092 terminates the coolant flow and step 5093 allows for removal of the heat exchange catheter from the patient.

Inducing hypothermia of the heart has been shown to reduce or prevent myocardial infarction effectively. By inducing hypothermia of the heart, the metabolic rate of the damaged heart cells is slowed down. While hypothermia is induced, appropriate repairs to the heart can take place. Appropriate repairs to the heart may include one or more of the following: a) lytic agents to lessen or prevent infarction, b) spontaneous resorption, c) performance of coronary arterial bypass grafts (CABG) or d) usage of an arterial balloon to open the artery and then stent the artery. Inducement of hypothermia of the heart slows the metabolic rate of the damaged heart tissues to allow time for appropriate repairs to take effect. In some instances, the damaged tissue may even repair itself. In other instances, other heart tissues are saved from damage. The catheters 10, 1110, 1200, 1300 and 1400 are inserted into the superior or inferior vena cava of a patient, placing the heat exchange elements of the catheters 10, 1110, 1200, 1300 and 1400 in contact with the blood flowing to the heart. Coolant flowing in closed loop within the heat exchange elements cools the blood flowing to the heart without directly mixing with the blood. The catheters 10, 1110, 1200, 1300 and 1400 and their heat exchange elements are kept at or near the superior or inferior vena cava for a sufficient amount of time to affect the heart temperature. A temperature sensor 1111 (not shown) monitors the temperature of the heart. In one embodiment, the temperature sensor 1111 is attached to the shaft of the catheter 10, 1110, 1200, 1300 and 1400. While the temperature of the heart is being monitored, the caregiver may decide to terminate further heat exchange to the heart or to reduce the heat exchange rate. This can be accomplished by controlling the flow rate of the coolant either by reducing the pump rate or stopping the pump rate of the heater/chiller unit 1154. Additionally, the temperature of the coolant can be changed. An increase in coolant temperature will decrease cooling to the blood and vice versa. At the end of the procedure, it may become desirous to increase the heart temperature. Here, the coolant temperature can be increased by the heater/chiller unit 1154 so that the coolant adds heat to the blood flowing to the heart. When heat exchange to the heart is completed, the intravascular catheter can be removed from the patient.

A method for ameliorating the effects of myocardial infarction in a patient includes administering at least one antithrombotic agent to the patient and advancing a catheter (such as, but not limited to, the catheter disclosed in the present application) into the venous system of the patient. The catheter can be inserted through the neck, the chest or the groin. An insertion through the neck can be accomplished by inserting the catheter into the jugular vein. Similarly, a chest insertion can be done through the subclavian vein while a groin insertion is made via the femoral vein. Once inserted into the patient, the catheter is used to induce mild or moderate hypothermia in the patient by circulating a working fluid through the catheter without the fluid contacting the blood. In one embodiment, the catheter's heat exchange element is lodged in the superior vena cava of the patient. In another embodiment, the patient's heat exchange element is lodged in the inferior vena cava of the patient.

In another embodiment, a separate method for combating the effects of MI includes making a cooling catheter available to a cardiac interventionist, instructing the cardiac interventionist to advance the catheter into the venous system of the patient upon presentation of symptoms of myocardial infarction and instructing the cardiac interventionist to initiate coolant flow through the catheter to induce hypothermia in the patient. Additionally, instructions to the cardiac interventionist can include administering at least one antithrombotic agent to the patient. In one embodiment, the cooling catheter is the catheter 10, 1110 of the present invention.

In yet another embodiment, a separate method for obtaining regulatory approval for use of a cooling catheter to treat myocardial infarction includes submitting a request to market the catheter to treat myocardial infarction based on a clinical trial having, as a desired endpoint, at least a reduction in infarct volume of a test group of patients vis-à-vis a control group of patients, the clinical trial not having, as an endpoint, a showing of improved patient outcome. In one embodiment, the cooling catheter is the catheter 10, 1110 of the present invention. In another embodiment, the endpoint is shown using magnetic resonance imaging (MRI) to show infarct volume patients in both groups. In another embodiment, the endpoint is shown by means of measuring a predetermined enzyme in both patient groups. And, in yet another embodiment, the endpoint is shown by using magnetic resonance imaging (MRI) to show infarct volume patients in both groups and by means of measuring a predetermined enzyme in both patient groups.

Thus, an improved heat transfer catheter is disclosed. While embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. A catheter adapted to exchange heat with a body fluid flowing through a body conduit, the catheter comprising
   an elongate body;
   at least one input lumen;
   at least one output lumen;
   at least one elongate element including a heat transfer lumen extending longitudinally therethrough with first and second ends, each heat transfer lumen being in fluid communication with one of the at least one input lumen at the first end and in fluid communication with one of the at least one output lumen at the second end, each of the at least one elongate element further including a portion between the first and second ends forming multiple turns, each turn of a plurality of the multiple turns having a length, being bonded to the elongate body along a fraction of the length and being otherwise displaced from the elongate body.

2. The catheter of claim 1, the lengths of the turns of the plurality of the turns being substantially equal.

3. The catheter of claim 1, the turns of the plurality of the turns being of two sets, the lengths of the first set being equal, the lengths of the second set being equal and the lengths of the first set being unequal with the lengths of the second set.

4. The catheter of claim 1, the elongate body lying within the plurality of the turns.

5. The catheter of claim 4, each turn of the plurality of the turns bonded along a fraction of the length at the elongate body being at only one location.

6. A catheter adapted to exchange heat with a body fluid flowing through a body conduit, the catheter comprising
   an elongate body;
   at least one input lumen;
   at least one output lumen;
   at least one elongate element including a heat transfer lumen extending longitudinally therethrough with first and second ends, each heat transfer lumen being in fluid communication with one of the at least one input lumen at the first end and in fluid communication with one of the at least one output lumen at the second end, each of the at least one elongate element further including a portion between the first and second ends forming a helix of multiple turns and extending longitudinally of the elongate body, each turn of a plurality of the turns having a length, being bonded to the elongate body along a fraction of the length and being otherwise displaced from the elongate body.

7. The catheter of claim 6, the lengths of the turns of the plurality of the turns being substantially equal.

8. The catheter of claim 6, the turns of the plurality of the turns being of two sets, the lengths of the first set being equal, the lengths of the second set being equal and the lengths of the first set being unequal with the lengths of the second set.

9. The catheter of claim 6, the elongate body lying within the plurality of the turns.

10. The catheter of claim 9, each turn of the plurality of the turns bonded along a fraction of the length at the elongate body being at only one location.

11. The catheter of claim 6 further comprising an infusion lumen extending with the at least one input lumen and the at least one output lumen.

12. The catheter of claim 11, the infusion lumen being through the elongate body.

13. The catheter of claim 12, one of the at least one input lumen and the at least one output lumen being through the elongate body.

14. The catheter of claim 12, at least one of the at least one input lumen being through the elongate body.

15. The catheter of claim 6, one of the at least one input lumen and the at least one output lumen being through the elongate body.

16. The catheter of claim 15, the at least one input lumen being through the elongate body.

17. The catheter of claim 6, each turn of the plurality of turns having a pitch substantially shorter than the lengths.

18. The catheter of claim 6, the at least one input lumen and the at least one output lumen extending within the elongate body.

19. The catheter of claim 6, the at least one elongate element being thin-walled and collapsible under fluid pressure of the body fluid with the heat transfer lumen at atmospheric pressure.

20. The catheter of claim 6, the at least one elongate element and the at least one input lumen having substantially equal cross-sectional areas.

21. A catheter adapted to exchange heat with a body fluid flowing through a body conduit, the catheter comprising
   an elongate body;
   an input lumen;
   an output lumen;
   an elongate element including a heat transfer lumen extending longitudinally therethrough with first and second ends, the heat transfer lumen being in fluid communication with the input lumen at the first end and in fluid communication with the output lumen at the second end, the elongate element further including a first portion between the first and second ends forming a helix of multiple turns extending longitudinally of the elongate body, the elongate element and the input lumen having substantially equal cross-sectional areas, a plurality of the turns each forming a loop area substantially greater than the major cross-sectional dimension of the elongate body when inflated.

22. The catheter of claim 21, the plurality of the turns each having a length, being bonded to the elongate body along a fraction of the length and being otherwise displaced from the elongate body.

23. The catheter of claim 21, the lengths of each of the plurality of the turns being substantially equal.

24. The catheter of claim 21, the elongate body lying within the plurality of the turns.

25. The catheter of claim 24, the plurality of the turns each being bonded only at one location to the elongate body.

26. The catheter of claim 21 further comprising an infusion lumen extending with the input lumen and the output lumen.

27. The catheter of claim 21, the elongate element being thin-walled and collapsible under fluid pressure of the body fluid with the heat transfer lumen at atmospheric pressure.

28. A catheter adapted to exchange heat with a body fluid flowing through a body conduit, the catheter comprising an elongate body allowing fluid flow therethrough;

a helical elongate element extending about at least a part of the body and in fluid communication therewith, the helical elongate element extending such that the body fluid can flow between the element and the body to exchange heat with the working fluid.

29. The catheter of claim 28, the elongate body including a supply lumen in fluid communication with the helical elongate element.

30. The catheter of claim 29, the supply lumen extending distally and the helical elongate element extending proximally from the supply lumen.

31. The catheter of claim 28, the helical elongate element extending in turns about the elongate body, at least two turns having bond points and being bonded at the bond points to the elongate body.

32. The catheter of claim 28 further comprising infusion lumens extending through the elongate body;

infusion ports in fluid communication with the infusion lumens, respectively, and displaced axially of the elongate body.

33. The catheter of claim 28 further comprising a proximal hub engaged with the elongate body and establishing at least one suture anchor.

34. The catheter of claim 33 further comprising a heater/chiller communicating with the elongate body through the proximal hub to heat/cool the flow therethrough.

35. A method for treating cardiac arrest in a patient comprising defibrillating the patient;

lowering the patient's temperature using at least one catheter placed in the venous system of the patient by circulating coolant through the catheter while the catheter is positioned in the patient's central venous system, such that the coolant does not enter the patient's bloodstream, wherein the catheter comprises:

an elongate body;

at least one input lumen;

at least one output lumen;

at least one elongate element including a heat transfer lumen extending longitudinally therethrough with first and second ends, each heat transfer lumen being in fluid communication with one of the at least one input lumen at the first end and in fluid communication with one of the at least one output lumen at the second end, each of the at least one elongate element further including a portion between the first and second ends forming multiple turns, each turn of a plurality of the multiple turns having a length, being bonded to the elongate body along a fraction of the length and being otherwise displaced from the elongate body.

36. The method of claim 35 further comprising administering a precordial thump to the patient.

37. The method of claim 35 further comprising ventilating the patient.

38. A method for treating cardiac arrest in a patient comprising administering a precordial thump to the patient;

lowering the patient's temperature using at least one catheter placed in the venous system of the patient by circulating coolant through the catheter while the catheter is positioned in the patient's central venous system, such that the coolant does not enter the patient's bloodstream, wherein the catheter comprises:

an elongate body;

at least one input lumen;

at least one output lumen;

at least one elongate element including a heat transfer lumen extending longitudinally therethrough with first and second ends, each heat transfer lumen being in fluid communication with one of the at least one input lumen at the first end and in fluid communication with one of the at least one output lumen at the second end, each of the at least one elongate element further including a portion between the first and second ends forming multiple turns, each turn of a plurality of the multiple turns having a length, being bonded to the elongate body along a fraction of the length and being otherwise displaced from the elongate body.

39. A method for treating myocardial infarction in a patient comprising identifying the patient has myocardial infarction;

lowering the patient's temperature using at least one catheter placed in the venous system of the patient by circulating coolant through the catheter while the catheter is positioned in the patient's central venous system, such that the coolant does not enter the patient's bloodstream, wherein the catheter comprises:

an elongate body;

at least one input lumen;

at least one output lumen;

at least one elongate element including a heat transfer lumen extending longitudinally therethrough with first and second ends, each heat transfer lumen being in fluid communication with one of the at least one input lumen at the first end and in fluid communication with one of the at least one output lumen at the second end, each of the at least one elongate element further including a portion between the first and second ends forming multiple turns, each turn of a plurality of the multiple turns having a length, being bonded to the elongate body along a fraction of the length and being otherwise displaced from the elongate body.

40. The method of claim 39 further comprising selecting a target temperature.

41. The method of claim 40 further comprising monitoring the target temperature; and adjusting the heater/chiller unit to provide coolant at a coolant temperature in accordance with the target temperature.

42. A method for treating myocardial infarction in a patient comprising identifying that the patient has myocardial infarction;

selecting a target temperature;

measuring the patient's temperature;

lowering the patient's temperature using at least one catheter placed in the venous system of the patient by circulating coolant through the catheter while the catheter is positioned in the patient's central venous system, such that the coolant does not enter the patient's bloodstream, wherein the catheter comprises:

an elongate body;

at least one input lumen;

at least one output lumen;

at least one elongate element including a heat transfer lumen extending longitudinally therethrough with first and second ends, each heat transfer lumen being in fluid communication with one of the at least one input lumen at the first end and in fluid communication with one of the at least one output lumen at the second end, each of the at least one elongate element further including a portion between the first and second ends forming multiple turns, each turn of a plurality of the multiple turns having a length, being bonded to the elongate body along a fraction of the length and being otherwise displaced from the elongate body;

adjusting the coolant temperature based on the patient's temperature.

43. The method of claim 42 further comprising removing the catheter from the patient once the target temperature is reached.

44. The method of claim 42 wherein the catheter is inserted into the jugular vein.

45. The method of claim 42 wherein the catheter is inserted into the subclavian vein.

46. A method for ameliorating the effects of myocardial infarction (MI) in a patient, comprising administering at least one antithrombotic agent to the patient;

advancing a catheter into the venous system of the patient; and inducing mild or moderate hypothermia in the patient by circulating a working fluid through the catheter without the fluid contacting the blood.

47. A method for combating the effects of myocardial infarction, comprising making a cooling catheter available to a cardiac interventionist;

instructing the cardiac interventionist to advance the catheter into the venous system of the patient upon presentation of symptoms of myocardial infarction; and instructing the cardiac interventionist to initiate coolant flow through the catheter to induce hypothermia in the patient.

48. The method of claim 47, further comprising instructing the cardiac interventionist to administer at least one antithrombotic agent to the patient.

* * * * *